US006284539B1

(12) United States Patent
Bowen et al.

(10) Patent No.: US 6,284,539 B1
(45) Date of Patent: Sep. 4, 2001

(54) METHOD FOR GENERATING DOPAMINERGIC CELLS DERIVED FROM NEURAL PRECURSORS

(75) Inventors: David C. Bowen, Washington, DC (US); Karl K. Johe, Potomac, MD (US)

(73) Assignee: NeuralStem Biopharmaceuticals, Ltd., College Park, MD (US)

( * ) Notice: Subject to any disclaimer, the term of this patent is extended or adjusted under 35 U.S.C. 154(b) by 0 days.

(21) Appl. No.: 09/169,309

(22) Filed: Oct. 9, 1998

(51) Int. Cl.[7] .................. C12N 15/63; C12N 15/85; C12N 15/87; C12N 15/00; C12N 15/09

(52) U.S. Cl. .................. 435/455; 435/320.1; 435/325; 435/368; 424/93.21; 514/44; 536/23.1; 536/23.5

(58) Field of Search .................. 435/467, 368, 435/320.1, 325, 455; 514/44; 424/93.21; 536/23.1, 23.5

(56) References Cited

U.S. PATENT DOCUMENTS 6,071,889 * 6/2000 Weiss et al. .................. 514/44

FOREIGN PATENT DOCUMENTS

WO94/04675 3/1994 (WO).

OTHER PUBLICATIONS

Carpenter et al, 1997, Exp. Neurol., 148: 187–204.*
Hall et al, 1992, An Introduction to Molecular Neurobiology, p 357.*
Ling et al, 1998, Exp. Neurol., 149: 411–423.*
Saucedo–Cardenas et al, 1998, PNAS, 95: 4013–4018.*
Stemple et al, 1997, Neuron, 18:1–4.*
Wagner et al, 1999, Nat. Biotech., 17: 653–659.*
Castillo et al., Mol. Cell. Neurosci. 11:36–46 (1998).
Castillo et al., Genomics 41:250–257 (1997).
Honkaniemi et al., Mol. Brian Res. 28:157–163 (1995).
Law et al., Gene Expr. 4:77–84 (1994).
Ling et al., Exp. Neurol. 149:411–423 (1998).
Mages et al., Mol. Endocrinol. 8:1583–1591 (1994).
Ohkura et al., Biochim. Biophys. Acta 1308:205–214 (1996).
Okabe et al., J. Immunol. 154:3871–3879 (1995).
Pena de Ortiz et al., Mol. Brain Res. 38:1–13 (1996).
Perrone–Capano et al., Bioessays 18:817–824 (1996).
Saucedo–Cardenas et al., Gene 187:135–139 (1997).
Saucedo–Cardenas et al., Proc. Natl. Acad. Sci. USA 95:4013–4018 (1998).
Scearce et al., J. Biol. Chem. 268:8855–8861 (1993).
Schapira, Baillieres Clin. Neurol. 6:15–36 (1997).
Unsicker et al., Ciba Found. Symp. 196:70–84 (1996).
Wang et al., Nat. Med. 1:1184–1188 (1995).
Xing et al., Mol. Brain Res. 47:251–261 (1997).
Ye et al., Cell 93:755–766 (1998).
Zetterstrom et al., Science 276:248–250 (1997).

* cited by examiner

*Primary Examiner*—Scott D. Priebe
*Assistant Examiner*—Peter Paras, Jr.
(74) *Attorney, Agent, or Firm*—Bell, Boyd & Lloyd LL

(57) ABSTRACT

The present invention describes a novel method to direct a particular set of fate choice decisions by multipotential precursor cells from the central nervous system. Specifically we show that introducing the gene coding for the nuclear receptor, Nurr1, into central nervous system (CNS) stem cells causes cells to adopt a dopaminergic cell fate. One use of this technology would be to prepare in vitro neural populations enriched in dopaminergic cells for transplantation in Parkinson's Disease or other neurological disorders. Furthermore, the finding that Nurr1 expression induces a dopaminergic phenotype suggests that introducing this gene into the brains of patients in which dopaminergic cells are degenerating or have been injured may promote the functional recovery of these neurons and thus the clinical recovery of the patient. Finally, the technology described in this application could be incorporated into a program of drug screening or gene discovery.

7 Claims, 23 Drawing Sheets

FIG. 1B1

```
          10         20         30         40         50
ATGCCCGACTACAAGGACGACGATGACAAGCCTTGTGTTCAGGCGCAGTA
 M  P  D  Y  K  D  D  D  D  K  P  C  V  Q  A  Q  Y>

60         70         80         90        100
TGGGTCCTCGCCTCAAGGAGCCAGCCCCGCTTCTCAGAGCTACAGTTACC
 G  S  S  P  Q  G  A  S  P  A  S  Q  S  Y  S  Y>

110        120        130        140        150
ACTCTTCGGGAGAATACAGCTCCGATTTCTTAACTCCAGAGTTTGTCAAG
 H  S  S  G  E  Y  S  S  D  F  L  T  P  E  F  V  K>

160        170        180        190        200
TTTAGCATGGACCTCACCAACACTGAAATTACTGCCACCACTTCTCTCCC
 F  S  M  D  L  T  N  T  E  I  T  A  T  T  S  L  P>

210        220        230        240        250
CAGCTTCAGTACCTTTATGGACAACTACAGCACAGGCTACGACGTCAAGC
 S  F  S  T  F  M  D  N  Y  S  T  G  Y  D  V  K>

260        270        280        290        300
CACCTTGCTTGTACCAAATGCCCCTGTCCGGACAGCAGTCCTCCATTAAG
 P  P  C  L  Y  Q  M  P  L  S  G  Q  Q  S  S  I  K>

310        320        330        340        350
GTAGAAGACATTCAGATGCACAACTACCAGCAACACAGCCACCTGCCCCC
 V  E  D  I  Q  M  H  N  Y  Q  Q  H  S  H  L  P  P>

360        370        380        390        400
TCAGTCCGAGGAGATGATGCCACACAGCGGGTCGGTTTACTACAAGCCCT
 Q  S  E  E  M  M  P  H  S  G  S  V  Y  Y  K  P>

410        420        430        440        450
CTTCGCCCCCGACACCCAGCACCCCGAGCTTCCAGGTGCAGCATAGCCCG
 S  S  P  P  T  P  S  T  P  S  F  Q  V  Q  H  S  P>

460        470        480        490        500
ATGTGGGACGATCCGGGCTCCCTTCACAACTTCCACCAGAACTACGTGGC
 M  W  D  D  P  G  S  L  H  N  F  H  Q  N  Y  V  A>
```

FIG. 1B2

```
       510        520        530        540        550
CACTACGCATATGATCGAGCAGAGGAAGACACCTGTCTCCCGCCTGTCAC
  T   T   H   M   I   E   Q   R   K   T   P   V   S   R   L   S>

560        570        580        590        600
TCTTCTCCTTTAAGCAGTCGCCCCCGGGCACTCCTGTGTCTAGCTGCCAG
  L   F   S   F   K   Q   S   P   P   G   T   P   V   S   S   C   Q>

610        620        630        640        650
ATGCGCTTCGACGGGCCTCTGCACGTCCCCATGAACCCGGAGCCCGCGGG
  M   R   F   D   G   P   L   H   V   P   M   N   P   E   P   A   G>

660        670        680        690        700
CAGCCACCACGTAGTGGATGGGCAGACCTTCGCCGTGCCCAACCCCATTC
  S   H   H   V   V   D   G   Q   T   F   A   V   P   N   P   I>

710        720        730        740        750
GCAAGCCGGCATCCATGGGCTTCCCGGGCCTGCAGATCGGCCACGCATCG
  R   K   P   A   S   M   G   F   P   G   L   Q   I   G   H   A   S>

760        770        780        790        800
CAGTTGCTTGACACGCAGGTGCCCTCGCCGCCGTCCCGGGGCTCTCCCTC
  Q   L   L   D   T   Q   V   P   S   P   P   S   R   G   S   P   S>

810        820        830        840        850
CAATGAGGGTCTGTGCGCTGTTTGCGGTGACAACGCGGCCTGTCAGCACT
  N   E   G   L   C   A   V   C   G   D   N   A   A   C   Q   H>

860        870        880        890        900
ACGGTGTTCGCACTTGTGAGGGCTGCAAAGGTTTCTTTAAGCGCACGGTG
  Y   G   V   R   T   C   E   G   C   K   G   F   F   K   R   T   V>

910        920        930        940        950
CAAAAAAACGCGAAATATGTGTGTTTAGCAAATAAAAACTGCCCAGTGGA
  Q   K   N   A   K   Y   V   C   L   A   N   K   N   C   P   V   D>

960        970        980        990       1000
CAAGCGCCGCCGAAATCGTTGTCAGTACTGTCGGTTTCAGAAGTGCCTAG
  K   R   R   R   N   R   C   Q   Y   C   R   F   Q   K   C   L>
```

FIG. 1B3

```
      1010       1020       1030       1040       1050
CTGTTGGGATGGTTAAAGAAGTGGTTCGCACGGACAGTTTAAAAGGCCGG
 A  V  G  M  V  K  E  V  V  R  T  D  S  L  K  G  R>

1060       1070       1080       1090       1100
AGAGGTCGTTTACCCTCGAAGCCGAAGAGCCCACAGGATCCCTCTCCCCC
 R  G  R  L  P  S  K  P  K  S  P  Q  D  P  S  P  P>

1110       1120       1130       1140       1150
CTCACCTCCGGTGAGTCTGATCAGTGCCCTCGTCAGAGCCCACGTCGATT
 S  P  P  V  S  L  I  S  A  L  V  R  A  H  V  D>

1160       1170       1180       1190       1200
CCAATCCGGCAATGACCAGCCTGGACTATTCCAGGTTCCAGGCAAACCCT
 S  N  P  A  M  T  S  L  D  Y  S  R  F  Q  A  N  P>

1210       1220       1230       1240       1250
GACTATCAGATGAGTGGAGATGATACCCAACATATCCAGCGGTTCTACGA
 D  Y  Q  M  S  G  D  D  T  Q  H  I  Q  R  F  Y  D>

1260       1270       1280       1290       1300
TCTCCTGACCGACTCTATGGAGATCATCAGAGGGTGGGCAGAGAAGATGC
  L  L  T  D  S  M  E  I  I  R  G  W  A  E  K  M>

1310       1320       1330       1340       1350
CTGGCTTTGCTGACCTGCCCAAAGCCGACCAGGACCTGCTTTTTGAATCA
 P  G  F  A  D  L  P  K  A  D  Q  D  L  L  F  E  S>

1360       1370       1380       1390       1400
GCTTTCTTAGAATTATTTGTTCTGCGCTTAGCATACAGGTCCAACCCAGT
 A  F  L  E  L  F  V  L  R  L  A  Y  R  S  N  P  V>

1410       1420       1430       1440       1450
GGAGGGTAAACTCATCTTTTGCAATGGGGTGGTCTTGCACAGGTTGCAAT
 E  G  K  L  I  F  C  N  G  V  V  L  H  R  L  Q>

1460       1470       1480       1490       1500
GCGTGCGTGGCTTTGGGGAATGGATTGATTCCATTGTTGAATTCTCCTCC
 C  V  R  G  F  G  E  W  I  D  S  I  V  E  F  S  S>
```

FIG. 1B4

```
         1510       1520       1530       1540       1550
     AACTTGCAGAATATGAACATCGACATTTCTGCCTTCTCCTGCATTGCTGC
       N  L  Q  N  M  N  I  D  I  S  A  F  S  C  I  A  A>

1560       1570       1580       1590       1600
     CCTGGCTATGGTCACAGAGAGACACGGGCTCAAGGAACCCAAGAGAGTGG
       L  A  M  V  T  E  R  H  G  L  K  E  P  K  R  V>

1610       1620       1630       1640       1650
     AAGAGCTACAAAACAAAATTGTAAATTGTCTTAAAGACCATGTGACTTTC
       E  E  L  Q  N  K  I  V  N  C  L  K  D  H  V  T  F>

1660       1670       1680       1690       1700
     AATAATGGGGGTTTGAACCGACCCAACTACCTGTCTAAACTGTTGGGGAA
       N  N  G  G  L  N  R  P  N  Y  L  S  K  L  L  G  K>

1710       1720       1730       1740       1750
     GCTGCCAGAACTCCGCACCCTTTGCACACAGGGCCTCCAGCGCATTTTCT
       L  P  E  L  R  T  L  C  T  Q  G  L  Q  R  I  F>

1760       1770       1780       1790       1800
     ACCTGAAATTGGAAGACTTGGTACCACCACCAGCAATAATTGACAAACTT
       Y  L  K  L  E  D  L  V  P  P  P  A  I  I  D  K  L>

1810       1820
     TTCCTGGACACCTTACCTTTC
       F  L  D  T  L  P  F>
```

50 μm

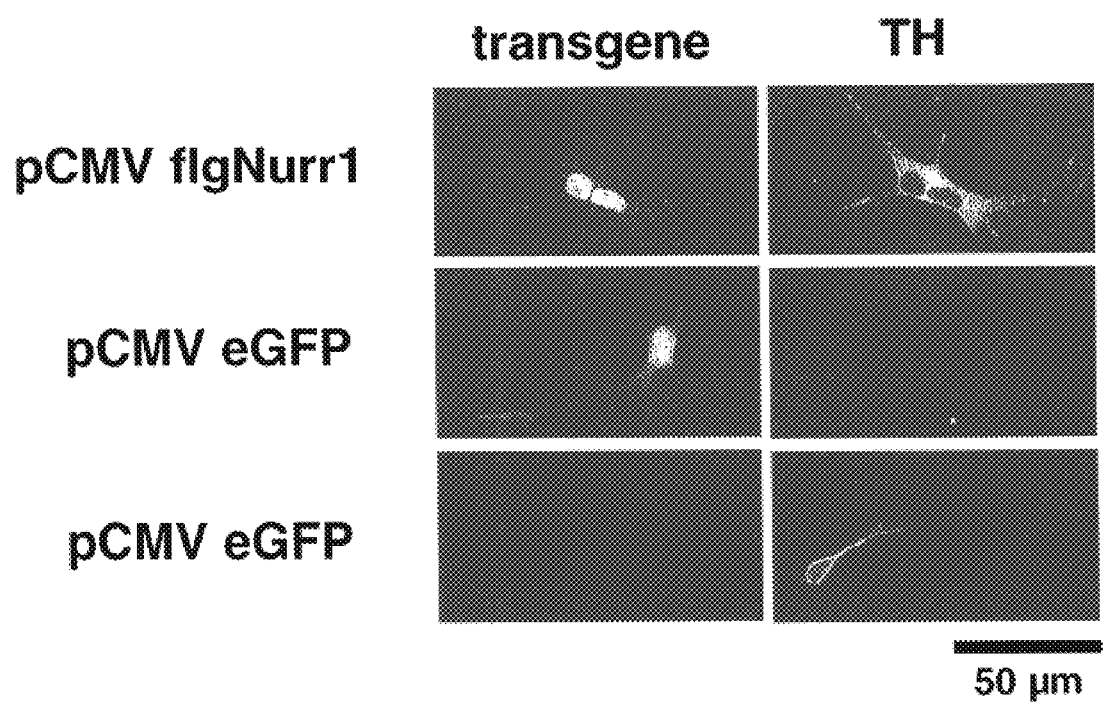

FIG. 6
MISS HIT
 Inactive Substance  Active Substance
MEASURE NURR1 EXPRESSION FIG. 7
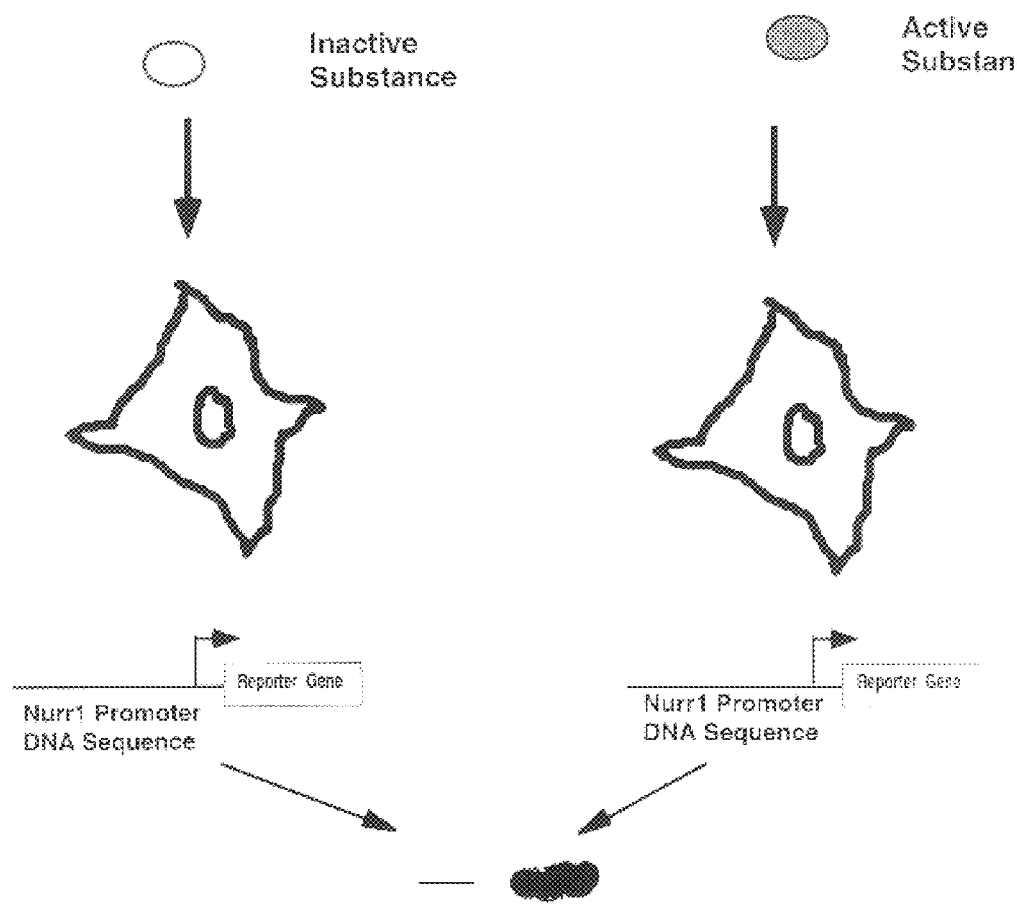
MEASURE REPORTER GENE EXPRESSION OR
MEASURE REPORTER GENE ACTIVITY

FIG. 9
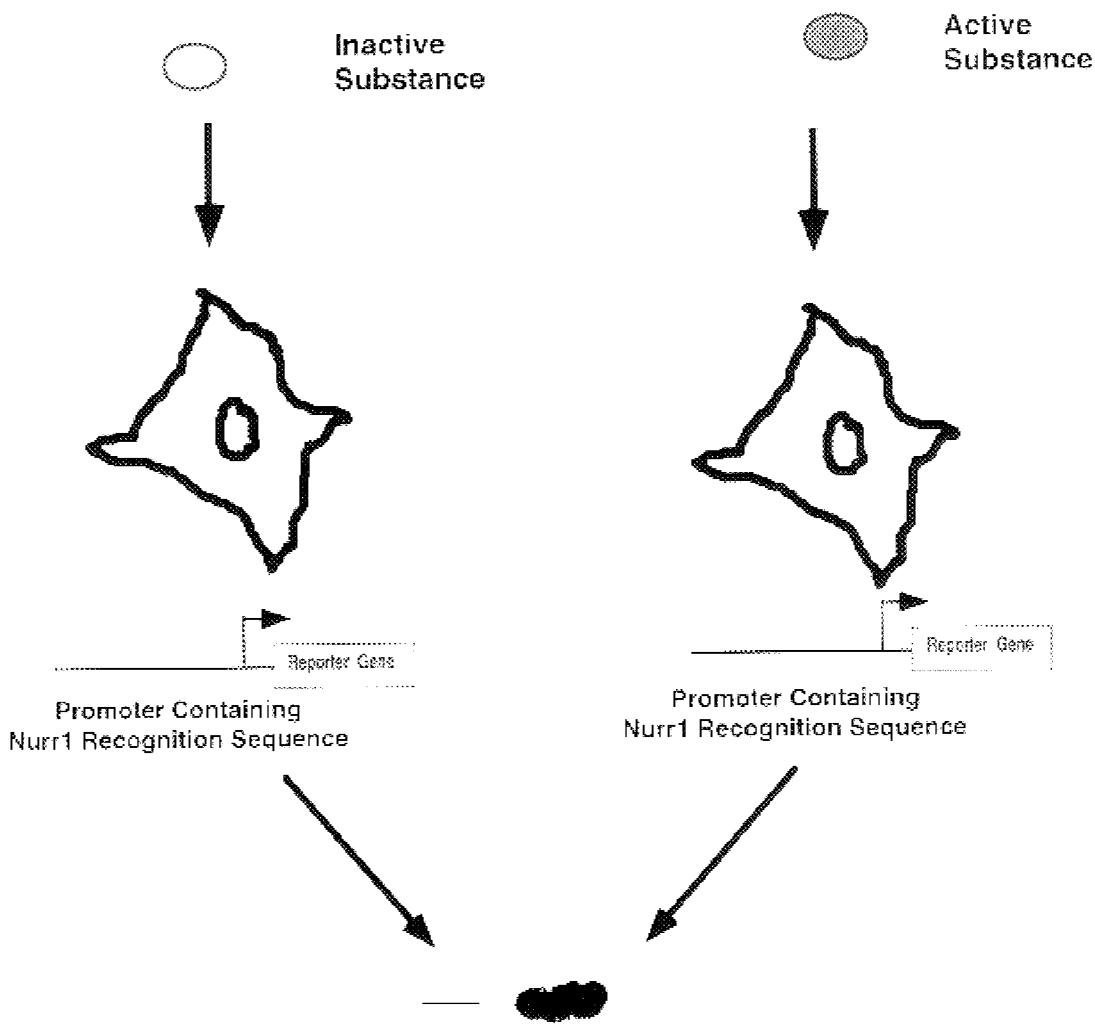
MEASURE REPORTER GENE EXPRESSION OR
MEASURE REPORTER GENE ACTIVITY Promoter Sequence Containing
Nurr1 Recognition Sequence FIG. 12
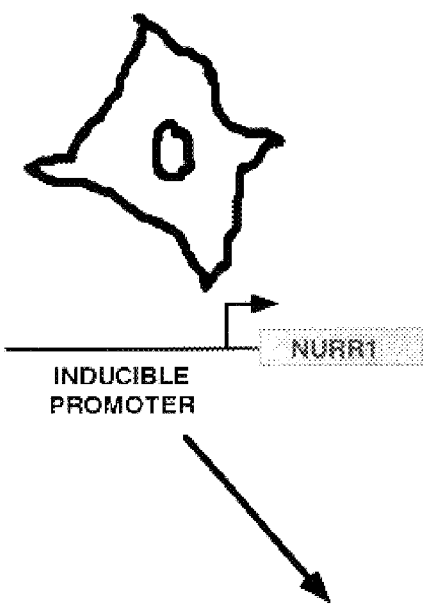
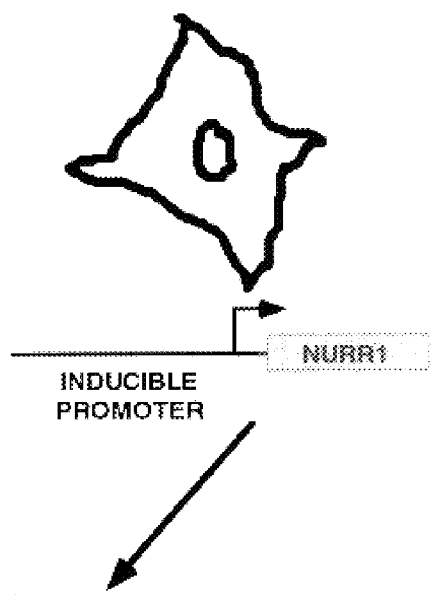
COMPARE GENE EXPRESSION

METHOD FOR GENERATING DOPAMINERGIC CELLS DERIVED FROM NEURAL PRECURSORS

BACKGROUND OF THE INVENTION

1. Field of the Invention

The present invention discloses a method for generating dopaminergic cells from a culture of mammalian CNS stem cells, methods for treating a patient with a neurological disorder, such as Parkinson's Disease, methods of screening for compounds which generate or increase the number of dopaminergic cells in a culture of mammalian CNS stem cells and methods for discovering genes involved in generating dopaminergic cells.

2. Description of the Related Art

A. Development of Dopaminergic Neurons

Generating the enormous cellular complexity of the mammalian central nervous system requires an intricate developmental program whose molecular mechanisms are only now beginning to be understood. This developmental program produces countless cell populations that are distinct in their morphology, function and/or biochemical characteristics. One such population has its cell bodies in the region of the ventral midbrain (VM) known as the substantia nigra pars compacta and projects to the striatum. These neurons are distinguished biochemically by the fact that they secrete dopamine as a neurotransmitter and thus express at high levels the enzyme tyrosine hydroxylase (TH) which catalyzes the rate-limiting step in the biosynthesis of dopamine[43].

Dopaminergic neurons are of enormous clinical significance because it is these cells that progressively lose function in patients with Parkinson's Disease (PD)[57]. The progressive loss of nigral dopaminergic function interferes with the normal working of the neuronal circuitry subserving motor control so that patients with PD show characteristic motor disturbances that typically consist of akinesia, rigidity and rest tremor but may also include pain, impaired olfaction, alterations of personality and depression[49]. Due to the potential clinical significance of such studies, much experimentation has been directed toward understanding the molecular mechanisms by which dopaminergic neurons develop.

One of the hallmarks of early embryonic development is the formation of the neural plate, a region of specialized ectoderm lying along the dorsal midline of the embryo. This neural plate subsequently develops a central depression and ultimately closes on itself to form the neural tube. The cells lining the interior of the tube then proliferate, differentiate and migrate to appropriate locations in the central nervous system. In the case of the cells destined to form the substantia nigra, mitotic precursor cells are generated near the midbrain/hindbrain junction. These cells then migrate radially to their ultimate position in the VM, where they differentiate into the various cells types found in the substantia nigra, the ventral tegmentum and the retrorubral nuclei[43].

The differentiation of the VM appears to be regulated in large part by inductive signals from the floor plate, a band of tissue that comprises the ventral midline of the developing mesencephalon. Removal of the floor plate results in the loss of dopaminergic neurons, among other cell types[21,47]. Conversely, replacement of a previously extirpated floor plate tube with an exogenous floor plate, though not with other cellular structures, restores the lost cellular phenotypes[68]. Similarly, addition of a supernumerary floor plate induces the ectopic formation of dopaminergic neurons[68].

Recent work has identified several genes that appear to play central roles in the differentiation of dopaminergic neurons in the VM. Several of these are described below while another, Nurr1, forms the subject of this application and will be discussed in a later section. Each of these genes is expressed in an appropriate temporal and spatial pattern to affect the differentiation of CNS stem cells into dopaminergic neurons in vivo. In addition, when each gene has been subjected to targeted disruption in mice, the resultant phenotypes have all shown distortions of normal VM patterning including aberrant differentiation of dopaminergic neurons.

One molecular signal responsible for the ability of the floor plate to influence the formation of dopaminergic neurons appears to be the expression of the Shh gene by floor plate cells. Adding an Shh gene product to embryonic VM explants increases the number of dopaminergic cells in the explants[20,63]. Another soluble protein shown to have some activity in promoting a dopaminergic fate choice is fibroblast growth factor 8 (FGF-8). Dopaminergic neurons were induced to form in ectopic locations when embryonic midbrain explants were exposed to latex beads coated with FGF-8. This effect, however, was blocked by antibodies to Sonic Hedgehog, indicating that in the absence of Shh functions[69], FGF-8 alone could not direct precursor cells to adopt a dopaminergic fate.

As shown by the experiments described above, the Shh signaling cascade, perhaps augmented by FGF-8, appears to play a key role in inducing the formation of dopaminergic neurons. However, distinct from prior methods using these two genes, we have developed other methods to increase the number of dopaminergic cells present in CNS stem cell cultures by activating an endogenous transcriptional regulator, Nurr1, rather than by utilizing soluble proteins like Sonic Hedgehog or FGF-8.

B. Other Soluble Factors can Promote the Dopaminergic Phenotype

Interleukin-1 has been reported to increase the number of cells expressing tyrosine hydroxylase (TH) when applied to a culture of VM tissue, an effect that was potentiated by interleukin-11, leukemia inhibitory factor (LIF), and glial cell line-derived neurotrophic factor (GDNF) as well as by mesencephalic membrane fragments and striatal culture-conditioned media[31]. Similarly, co-culture of VM precursor cells with VM neurons is also reported to increase the number of dopaminergic cells[48]. In cultures of the IMR-32 neuroblastoma cells line, exposure to basic fibroblast growth factor (bFGF) caused these tumor-derived cells to express TH, an effect that was potentiated by ciliary neurotropic factor (CNTF)[50]. bFGF has also been claimed to promote an increase in TH-positive neurons from mixed cultures of VM precursors and neurons[34], as has ascorbic acid[24]. Similarly, while platelet-derived growth factor was found to increase the number of neurons derived from VM CNS stem cell cultures, it did not promote an increase in dopaminergic neurons[23].

Other factors have been shown to enhance the survival of dopaminergic neurons. For example, brain derived neurotrophic factor (BDNF), neurotrophin 4/5, glial derived neurotrophic factor (GDNF) and neurturin have been shown to promote the survival of dopaminergic neurons from rat or human midbrain. Both epidermal growth factor (EGF) and bFGF have been shown to enhance the survival of dopaminergic neurons although this appears to be due to the proliferative effect that these proteins have on glia rather than a direct action on neurons. Cytokines such as transforming growth factor-α (TGF-α), platelet derived growth factor, interleukin-1b, interleukin-6 and insulin-like growth factor-I have also been shown to promote the survival of dopaminergic neurons while insulin like growth factor II has been reported to increase neurite outgrowth from these cells. Non-proteinaceous factors such as GM1 ganglioside and cyclic AMP also increase dopaminergic neuron survival (reviewed in references 43 and 61).

In addition to the single factors described above, several complex mixtures or culture conditions have been shown to increase the survival of postmitotic dopaminergic neurons. These conditions include co-culturing VM neurons with striatal astrocytes or striatal cells or exposing VM neuronal cultures to striatal extract or striatal membranes. Similarly, conditioned media from cortical astrocytes, the B49 glial cell line, the R33 neural retina glial cell line, the mesencephalic glial cell line Mes42 and the JS1 Schwannoma cell line have all been reported to increase the survival of dopaminergic neurons as has an uncharacterized 14 kDa protein upregulated by retinoic acid (reviewed in references 43 and 61).

C. Nurr1 is Required for the Differentiation of Dopaminergic Neurons

Several recent reports[2,54,70] demonstrate that the transcription factor Nurr1 is required for the development and/or survival of dopaminergic neurons in vivo. Nurr1 is a member of the nuclear receptor superfamily which consists of proteins capable of binding to short defined sequences of DNA and activating the transcription of target genes downstream of the recognized sequence[13]. The activity of many members of this family is regulated by binding a specific ligand, such as estrogen for the estrogen receptor, in the presence of which the transcriptional activity of the nuclear receptor is markedly upregulated. Though Nurr1 shares a broad sequence homology with other members of this family, no activating ligand has yet been reported for this receptor, although the DNA sequence to which it binds has been identified as AAAGGTCA[56].

Nurr1 was originally identified[27] by screening a mouse brain cDNA library at low stringency with a probe derived from the DNA binding region of COUP-TF, another member of the nuclear receptor superfamily[62]. Although it is part of the large nuclear receptor superfamily, Nurr1 comprises part of a much smaller subfamily of related genes, consisting of Nurr-1, Nur77 (using the nomenclature of the mouse genes) as well as NOR-1 and NOR-2 (cloned from rat). Each of these genes has been derived independently from a multiplicity of sources and has a corresponding diversity of names. Thus, homologues of Nurr1 have been isolated from mouse genomic libraries[3,53], rat liver (where it was called RNR-1[56]), a rat hippocampal library (where it was called HZF-3[42]), a human lymphoid cell line (where it was called TINUR[40]) and human T cells (where it was called NOT[33]). Nurr1 is highly homologous to Nur77, a protein originally identified in a screen for genes induced rapidly by serum in mouse fibroblasts[15]. Nur77 was also been independently identified[26] and then cloned[35] from rat PC12 cells as a gene upregulated by exposure to nerve growth factor and was thus termed NGFI-B (alternately, NGF1β). Homologues of Nur77 have subsequently been cloned from human (where it was called NAK-1[36] or TR3[4]), mouse (where it was called N10[52]), and dog[46]. EST fragments of NAK-1[16-18,37] or NAK-1 and TINUR[18] have also been cloned. In addition, two related genes, NOR-1 and NOR-2, have recently been isolated from apoptotic rat forebrain neurons in culture[38] and rat brain[45], respectively. NOR-1 has subsequently been cloned from human fetal brain[39]. The nuclear receptors CNR8 from *Caenorhabditis elegans*, BHR38 from *Bombyx mori*[60] and DHR38 from *Drosophila melanogaster*[60] are also thought to belong to this subfamily. Finally, gene fragments with sequence homology to Nurr1 have also been cloned from *Danio rerio* and *Petromyzon marinus*[7].

Nurr1 is expressed predominantly in the CNS[27] where in the adult rat it is expressed at high levels in numerous brain regions, including the substantia nigra pars compacta but not the neighboring pars reticulata[66,71]. As detected by in situ hybridization, Nurr1 expression begins early in the embryonic development of the brain with strong expression seen in the developing midbrain at embryonic day 10.5 in the mouse[70] which is before dopaminergic neurons differentiate. At embryonic day 18, Nurr1 expression is strong in the ventral midbrain where expression persists until adulthood[71]. In the adult hippocampus, Nurr1 mRNA is strikingly upregulated by drugs that induce seizures[42,67] or lesions[19].

The developmentally regulated pattern of Nurr1 expression just described suggested that this gene might play an important role in aspects of neural development. For this reason, experiments were undertaken[2,54,70] to create targeted disruptions of the Nurr1 gene in mice. Mice lacking both copies of Nurr1 develop in utero to term and are born alive. However, they fail to suckle and die shortly after birth[2,54,70]. Histological analysis reveals that while wild-type litter mate controls show abundant expression of TH mRNA2,54,70, as well as TH and aromatic acid decarboxylase protein[2], Nurr-1–/–mice show none of these markers of differentiated dopaminergic neurons[2,54,70]. Interestingly, the development of the VM is not completely perturbed in these mice. At embryonic day 11.5, prior to the generation of dopaminergic neurons, the ventral midbrain of Nurr-1–/– mice expresses the homeobox protein Ptx-3[54] which is an early marker for cells that later become dopaminergic[58]. While this protein continues to be expressed at high levels in the VM of wild-type mice, its expression is virtually lost in the Nurr-1–/–mice[54]. Significantly, in the Nurr1 null mice, dopaminergic neurons are absent only in VM while other brain regions containing dopaminergic neurons are unaffected[2,54,70]. Whether this phenotype results from the death of dopaminergic neurons[54,70] or a failure of these cells to differentiate[2] remains disputed.

Though the experiments just described show that Nurr1 is required for at least some stage(s) of dopaminergic neural differentiation or survival, these results do not predict whether Nurr1 is sufficient to confer a dopaminergic phenotype on CNS stem cells or other neural precursors. Frequently, activating or repressing transcription factor function alters cellular physiology in unpredictable and non-obvious ways. For example, suppressing the activity of the crx gene in the retina decreases the number of bipolar cells and inhibits rod outer segment formation. Unexpectedly, overexpression of the crx gene in the retina leads to an increased number of photoreceptors, but has no effect on bipolar cell fate choice[11,12]. To take another example, the transcription factor fosB was characterized as a gene that is rapidly upregulated by environmental stress in a variety of neuronal contexts. Paradoxically, targeted deletion of this gene in mice had no effect on the response of the mice to environmental stress. Rather, in a completely unpredicted manner, mice null for fosB display a total absence of normal maternal nurturing behavior[1]. Thus, a phenotype arising from deletion of a gene function cannot predict or anticipate the results of ectopic expression of the same gene in the same cellular context. The program of results described below show that ectopic expression of Nurr1 is sufficient to induce CNS stem cells or other neural precursor cells to adopt a dopaminergic cell fate.

The identification of NOT[33], the human homologue of Nurr1, has led to the filing of a patent application (WO 94/04675)[25] describing the DNA sequence of this protein as well as an anti-NOT antibody. While this patent application includes data to suggest possible roles for NOT in the development or function of the immune or hematopoietic system, WO 94/04675 presents no data or even discussion that would predict that Nurr1 is able to induce a dopaminergic phenotype in neural CNS stem cells, as shown by the results presented in this application.

The DNA sequence presented in WO 94/04675 was derived not from neural tissue but rather from human peripheral blood T-cells. Indeed, WO 94/04675 provides equivocal data on whether NOT is expressed in neural tissue. The inventors show that when mRNA from various tissues is hybridized with a probe derived from the NOT nucleic acid sequence, a strong band is detected from brain mRNA (WO 94/04675; FIG. 2C). However, when the inventors went on to test the expression of NOT mRNA in cell lines from various sources, the neural cell line they tested (IMR-32) showed no NOT expression, even after stimulation with phorbol myristate acetate, the ionophore A23187 and cycloheximide, conditions under which NOT is abundantly expressed in T-cells and fibroblasts (WO 94/04675; FIG. 2B). Thus, our current findings, as well as the applications derived from them, represent novel and non-obvious advances over the prior art as presented both in published reports and in WO 94/04675.

SUMMARY OF THE INVENTION

As stated above, the present invention discloses a method for generating dopaminergic cells from a culture of mammalian CNS stem cells, methods for treating a patient with a neurological disorder, such as Parkinson's Disease, methods of screening for compounds which generate or increase the number of dopaminergic cells in a culture of mammalian CNS stem cells and methods for discovering genes involved in generating dopaminergic cells.

More specifically, the method for generating dopaminergic cells in a culture of mammalian CNS stem cells comprises culturing mammalian CNS stem cells in vitro; introducing an exogenous gene encoding a transcriptional regulator into the mammalian CNS stem cells in the culture; incubating the mammalian CNS stem cells; and identifying dopaminergic cells in the culture.

In a preferred embodiment of the method, the exogenous gene encoding a transcriptional regulator is selected from the group consisting of Nurr1, RNR-1, HZF-3, TINUR, NOT, Nur77, NGF1-B, NAK-1, N10, NOR-1 and NOR-2. In a more preferred embodiment, the exogenous gene encoding a transcriptional regulator is Nurr1.

In another preferred embodiment, the method further comprises incubating the mammalian CNS stem cells with an agonist of protein kinase A activity. In a more preferred embodiment of the method, the agonist of protein kinase A activity is selected from the group consisting of forskolin; 1,9-dideoxy-forskolin; 6-[[(2-carbethoxyethyl)amino]carbonyl]-forskolin; 6-acetyl-7-deacetyl-forskolin; 6-O-[3'-(piperidino)propionyl]-forskolin hydrochloride; 7-deacetyl-forskolin; 7-deacetyl-6-(N-acetylglycyl)-forskolin; 7-deacetyl-7-[O-(N-methylpiperazino)-g-butyryl]-forskolin, dihydrochloride; 7-deacetyl-7-O-hemisuccinyl-forskolin; 3',5'cyclic monophosphate (cAMP); 8-chloro-cAMP; 8-bromo cAMP; 8-(4-chloropheylthio)-cAMP; dibutyryl-cAMP; dioctanoyl-cAMP; N6-monobutyryl-cAMP; adenosine 3', 5'cyclic monophosphorthioate, Sp-isomer; and 8-bromo-adenosine 3',5'cyclic monophosphorthioate, Sp-isomer. In a most preferred embodiment of the method, the agonist of protein kinase A activity is forskolin.

In another preferred embodiment of the method, the mammalian CNS stem cells are selected from ventral midbrain, dorsal midbrain, lateral ganglionic eminence, hippocampus, cerebral cortex, striatum, septum, diencephalon, mesencephalon, hindbrain and spinal cord. In a more preferred embodiment of the method, the mammalian CNS stem cells are human CNS stem cells.

A method for treating a patient with a neurological disorder comprises culturing mammalian CNS stem cells in vitro; introducing an exogenous gene encoding a transcriptional regulator into the mammalian CNS stem cells in the culture; identifying dopaminergic cells in the culture; and transplanting dopaminergic cells into the brain of a patient in need thereof.

In a preferred embodiment of the method, the exogenous gene encoding a transcriptional regulator is selected from the group consisting of Nurr1, RNR-1, HZF-3, TINUR, NOT, Nur77, NGF1-B, NAK-1, N10, NOR-1 and NOR-2. In a more preferred embodiment of the method, the exogenous gene encoding a transcriptional regulator is Nurr1.

In another preferred embodiment, the method further comprises incubating the mammalian CNS stem cells with an agonist of protein kinase A activity. In a more preferred embodiment of the method, the agonist of protein kinase A activity is selected from the group consisting of forskolin; 1,9-dideoxy-forskolin; 6-[[(2-carbethoxyethyl)amino]carbonyl]-forskolin; 6-acetyl-7-deacetyl-forskolin; 6-O-[3'-(piperidino)propionyl]-forskolin hydrochloride; 7-deacetyl-forskolin; 7-deacetyl-6-(N-acetylglycyl)-forskolin; 7-deacetyl-7-[O-(N-methylpiperazino)-g-butyryl]-forskolin, dihydrochloride; 7-deacetyl-7-O-hemisuccinyl-forskolin; 3',5'cyclic monophosphate (cAMP); 8-chloro-cAMP; 8-bromo cAMP; 8-(4-chloropheylthio)-cAMP; dibutyryl-cAMP; dioctanoyl-cAMP; N6-monobutyryl-cAMP; adenosine 3', 5'cyclic monophosphorthioate, Sp-isomer; and 8-bromo-adenosine 3',5'cyclic monophosphorthioate, Sp-isomer. In a most preferred embodiment of the method, the agonist of protein kinase A activity is forskolin.

In another preferred embodiment of the method, the mammalian CNS stem cells are selected from ventral midbrain, dorsal midbrain, lateral ganglionic eminence, hippocampus, cerebral cortex, striatum, septum, diencephalon, mesencephalon, hindbrain and spinal cord.

In more preferred embodiments of the method, the mammalian CNS stem cells are human CNS stem cells and the neurological disorder is Parkinson's Disease.

A method for treating a patient experiencing compromised dopaminergic function comprises introducing a Nurr1 gene into the brain of a patient experiencing compromised dopaminergic function. In a preferred embodiment of the method, the compromised dopaminergic function results from Parkinson's Disease.

Another method for treating a patient experiencing compromised dopaminergic function comprises administering a substance capable of upregulating Nurr1 expression or activity to a patient experiencing compromised dopaminergic function. In a preferred embodiment of the method, the compromised dopaminergic function results from Parkinson's Disease.

A method of screening for substances that increase Nurr1 expression comprises culturing cells endogenously expressing Nurr1; exposing the cultured cells to a substance of interest; and determining whether the substance increased the expression of Nurr1.

Another method of screening for substances that increase Nurr1 expression comprises introducing a construct comprising a Nurr1 promoter linked to a reporter gene into a culture of cells; exposing the cultured cells to a substance of interest; and determining whether the substance increased the expression of the reporter gene.

Another method of screening for substances that increase Nurr1 activity comprises introducing a construct comprising a Nurr1 response element (AAAGGTCA) linked to a reporter gene into a culture of cells, where the cells express Nurr1 either endogenously or due to the introduction of an exogenous Nurr1 gene; exposing the cultured cells to a substance of interest; and determining whether the substance increased expression of the reporter gene.

A method for identifying genes in a signalling pathway by which a cell acquires a dopaminergic phenotype comprises introducing a Nurr1 gene into a culture of cells; examining genes expressed in the cultures into which the Nurr1 gene has been introduced relative to genes expressed in cultures in which the Nurr1 gene has not been introduced; and identifying genes in the signalling pathway by which a cell acquires a dopaminergic phenotype.

Another methods for identifying genes in a signalling pathway by which a cell acquires a dopaminergic phenotype comprises introducing a construct comprising a Nurr1 coding sequence under control of an inducible promoter into a culture of cells; exposing the cells to an inducing agent capable of regulating expression of genes under the control of the inducible promoter or to an inactive control substance; comparing a complement of genes expressed in the cells that have been exposed to the inducing agent with a complement of genes expressed by the cells treated with the inactive control substance; and identifying genes in the signalling pathway by which a cell acquires a dopaminergic phenotype.

Another method for identifying genes in a signalling pathway by which a cell acquires a dopaminergic phenotype comprises introducing a construct coding for a chimeric protein in which a DNA binding domain of Nurr1 is fused to a ligand-binding domain of a nuclear receptor having a known activating ligand; exposing the cells to the activating ligand or to an inactive control substance; comparing a complement of genes expressed in the cells that have been exposed to the activating ligand with a complement of genes expressed by the cells treated with the inactive control substance; and identifying genes in the signalling pathway by which a cell acquires a dopaminergic phenotype.

Another method for identifying genes in a signalling pathway by which a cell acquires a dopaminergic phenotype comprises culturing cells that express Nurr1; exposing the cells to a substance capable of upregulating Nurr1 expression or activity or to an inactive control substance; comparing a complement of genes expressed in the cells that have been exposed to the substance capable of upregulating Nurr1 expression or activity with a complement of genes expressed by the cells treated with the inactive control substance; and identifying genes in the signalling pathway by which a cell acquires a dopaminergic phenotype.

BRIEF DESCRIPTION OF THE DRAWINGS

In FIG. 1(B1–B4), the nucleotide sequence encoding the recombinant flgNurr1 chimeric protein and the corresponding amino acid sequence of the recombinant flgNurr1 chimeric protein encoded by pCMVflgNurr1 are shown (SEQ ID NO:1). Standard one letter abbreviations for amino acids are used.

In FIG. 2, using indirect immunofluorescence, VM CNS stem cell cultures transfected either with pCMVflgNurr1 (top row) or pCMVeGFP (center and bottom rows) were doubly immunostained with anti-TH and anti-FLAG (top row) or stained for TH in the rhodamine channel and analyzed for eGFP expression by direct inspection in the fluorescein channel (center and bottom rows). The right hand column shows expression of TH while the left hand column shows the expression of the introduced transgene, either flgNurr1 (top row) or eGFP (center and bottom rows).

In FIG. 6, a first method of screening for substances that increase Nurr1 expression is shown.

In FIG. 7, a second example of a strategy to identify substances that increase Nurr1 expression is shown.

In FIG. 9, an example of a strategy to identify substances that increase Nurr1 activity is shown.

In FIG. 12, a second example of a strategy to identify genes in the signalling pathway by which a cell acquires a dopaminergic phenotype is shown.

DETAILED DESCRIPTION OF THE PREFERRED EMBODIMENTS

Figure 1A:
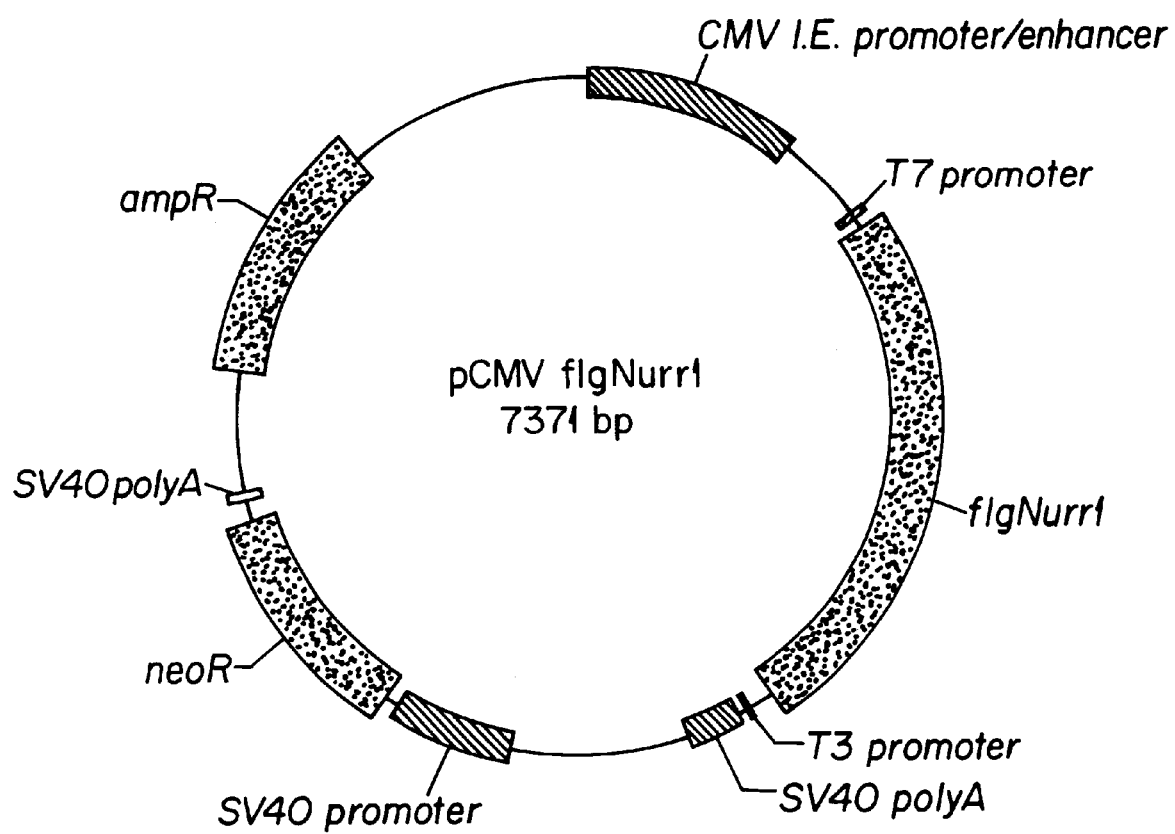
In FIG. 1A, a schematic map of the pCMVflgNurr1 construct is shown.

The present invention discloses a method for generating dopaminergic cells from a culture of mammalian CNS stem cells, a method for treating a patient with a neurological disorder, such as Parkinson's Disease, a method of screening for compounds which increase the number of dopaminergic cells in a culture of mammalian CNS stem cells and a method for discovering genes involved in generating dopaminergic cells.

1. MATERIALS AND METHODS

A. Materials mAb M2 against the FLAG epitope was purchased from Kodak Imaging Systems (Rochester, N.Y.), mAb AP-20 against MAP2a/b from Sigma (St. Louis, Mo.) and pAb sc-990 from Santa Cruz Biotechnology (Santa Cruz, Calif.). Antibody sc-990 was raised against a 20 amino acid peptide comprising the C-terminal of mouse Nurr1 and is mislabelled in the Santa Cruz catalogue where it is shown as an antibody to NGFI-B. A polyclonal antibody, P401, against TH was obtained from Pel-Freez (Rogers, Ark.). The pCM-VflgNurr1 construct was a generous gift of Dr. Vera Nikodem (National Institute of Diabetes and Digestive and Kidney Disease, Bethesda, Md.). The lipofectamine PLUS kit was purchased from Life Technologies, Inc. (Gaithersburg, Md.). Fluorophore-conjugated secondary antibodies were obtained from Vector Labs (Burlingame, Calif.) and peroxidase-labeled secondary antibodies were obtained from Promega (Madison, Wis.). General laboratory reagents were obtained from standard suppliers.

B. Cell Culture

COS cells were maintained under standard conditions in medium consisting of DMEM containing 2 mM L-glutamine, 100 U/ml penicillin/streptomycin and 10% fetal bovine serum. CNS stem cells were prepared according to published methods[22,23]. Briefly, embryonic tissue was dissected from embryonic day 12 rat ventral midbrain (VM) or dorsal midbrain (DM) or embryonic day 15 rat lateral ganglionic eminence (LGE), dissociated and cultured in N2a medium+10 ng/ml bFGF. (N2a medium: 50% DMEM, 50% Ham's F-12+100 $\mu$M putrescine, 30 nM sodium selenite, 20 nM progesterone, 25 $\mu$g/ml insulin, 100 $\mu$g/ml apotransferrin and 100 U/ml penicillin/streptomycin). Cells were expanded as necessary before replating onto coverslips for transfection. In some trials, CNS stem cell cultures had been cryogenically preserved prior to replating. All cells were maintained at 37° C. in 100% relative humidity and 5% $CO_2$/95% air.

C. Transfection

CNS stem cells were plated onto glass coverslips (22 mm×22 mm) coated with poly-ornithine and fibronectin, then cultured overnight in N2a medium+10 ng/ml bFGF. A transfection mix was prepared using the lipofectamine PLUS kit according to the manufacturer's directions. Cells were exposed to the transfection mix for 3 h, after which the transfection mix was removed and replaced with N2a medium without bFGF. In some experiments, cultures were treated with daily administration of 10 $\mu$M forskolin in DMSO or with DMSO alone.

D. Cell Staining

Cells were fixed in 4% buffered paraformaldehyde for 10 min, then rinsed in PBS and incubated in 5% goat serum in PBS containing 0.1% Triton (NGS/PBT) for 1 h. Primary antibody was then added overnight in NGS/PBT at 4° C., after which cells were washed 3× in PBS containing 0.1% Triton then incubated in fluorophore-conjugated secondary antibody 2 h at RT followed by 3 washes in PBS containing 0.1% Triton. Slides were mounted in glycerol containing 2% DABCO and viewed on a Nikon Eclipse fluorescence microscope.

E. Immunoprecipitation/Immunoblot

Two days after transfection, COS cells were washed 3× in cold PBS then scraped into 1 ml of cold extraction buffer consisting of PBS containing 20 $\mu$g/ml aprotinin, 1 mM PMSF, 1.25 mM EDTA and 0.1% NP-40. Extracts were incubated 15 min at 4° C., then centrifuged at 14000 rpm for 10 min. Supernatants were immunoprecipitated by standard protocols[14] with 5 $\mu$l/ml of pAb sc-990. Immunoprecipitates were electrophoresed by SDS-PAGE, transferred to Immobilon PVDF membranes (Millipore, Inc., South San Francisco, Calif.) and immunoblotted by standard techniques[14] first with mAb M2 then with a peroxidase-conjugated anti-mouse antibody, followed by enhanced chemiluminescence visualization. Alternately, extracts were immunoprecipitated with 2 $\mu$l/ml mAb M2 then immunoblotted with pAb sc-990.

2. EXAMPLES

A. Example 1

Figure 1C:
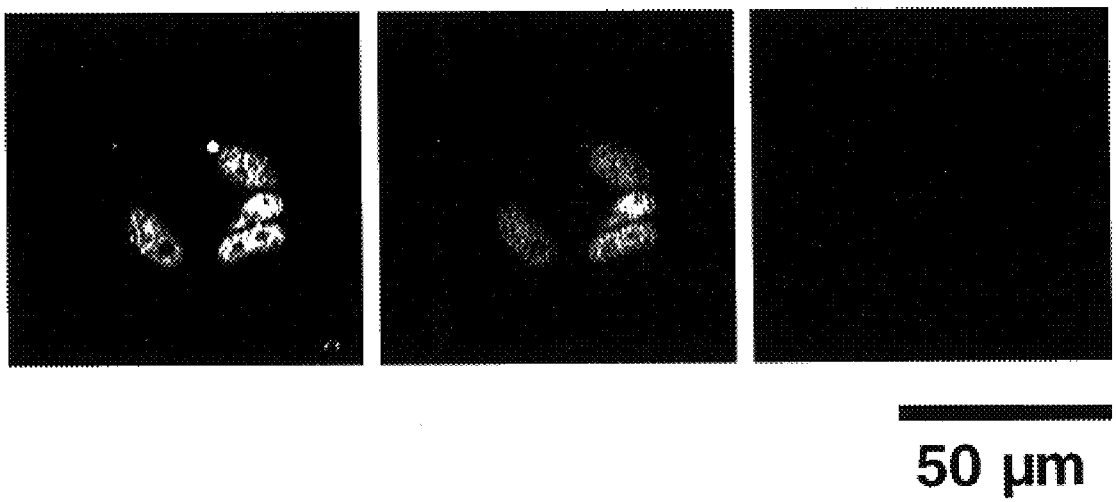
In FIG. 1C, COS-7 cells transfected with (left and center panels) or without (right panel) pCMVflgNurr1 were stained by indirect immunofluorescence with anti-FLAG mAb M2 (left panel) or anti-Nurr pAb sc-990 (center and right panels).

In order to express and detect Nurr1 in CNS stem cells, we utilized a recombinant construct coding for a chimeric Nurr1 protein in which the FLAG epitope (DYKDDDDK; SEQ ID NO:2) was inserted just subsequent to the start methionine (FIG. 1B). This sequence was subcloned into a pCI-neo vector (Promega; Madison, Wis.) to generate pCMV-flgNurr1. When this construct was transfected into COS cells, we found that the chimeric protein was expressed abundantly and was recognized by the M2 anti-FLAG monoclonal antibody by immunocytochemistry and on immunoblots. Thus, COS cells transfected with pCMVflgNurr1 generated a bright fluorescent signal that was confined to the nucleus when stained by indirect immunofluorescence using mAb M2 (FIG. 1C, left panel). The same cells showed coincident labelling with sc-990, an anti-Nurr1 polyclonal antibody (FIG. 1C, center panel), whereas untransfected cells stained in parallel gave no immunofluorescent signal (FIG. 1C, right panel). Similarly, no immunofluorescent signal was obtained from flgNurr1-transfected cells when the M2 antibody was omitted.

Figure 1D:
In FIG. 1D, immunoblots using mAb M2 were performed on cell extracts immunoprecipitated either with (center and right lanes) or without (left lane) pAb sc-990. Extracts were from cells transfected either with (left and center lanes) or without (right lane) pCMVflgNurr1.

To confirm that the protein recognized by mAb M2 was authentic Nurr1, we subjected extracts of COS cells transfected with pCMVflgNurr1 to immunoprecipitation with pAb sc-990 followed by immunoblot with mAb M2. As shown in FIG. 1D, this procedure yielded a single immunoreactive band migrating at the molecular weight ($\approx$80 kDa) predicted for flgNurr1 (center lane). This band was absent when untransfected COS cells were immunoprecipitated with the same antibody (right lane) or when pAb sc-990 was omitted from the immunoprecipitation (left lane). Using the same immunoprecipitation/immunoblot procedure, we obtained similar results to those just described when mAb M2 was used as the immunoprecipitating antibody and pAb sc-990 was used to immunoblot.

B. Example 2

Having shown that we could express and specifically detect flgNurr1, we then asked whether expression of this construct by CNS stem cells affected whether these cells adopted a dopaminergic phenotype. To this end, we established cultures of CNS stem cells from embryonic rat VM, then transfected these cells with pCMVflgNurr1 and stained the cultures for TH at varying times after transfection. When we examined cultures treated in this manner, we found numerous TH–immunoreactive (TH+) cells which also showed strong nuclear staining for flgNurr1 (FIG. 2, top row). By contrast, parallel cultures that were either sham-transfected or transfected with a control pCMV plasmid encoding enhanced green fluorescent protein (eGFP) contained only sporadic TH+ cells which did not express the eGFP transgene (FIG. 2, center and bottom rows).

C. Example 3

Figure 3A:
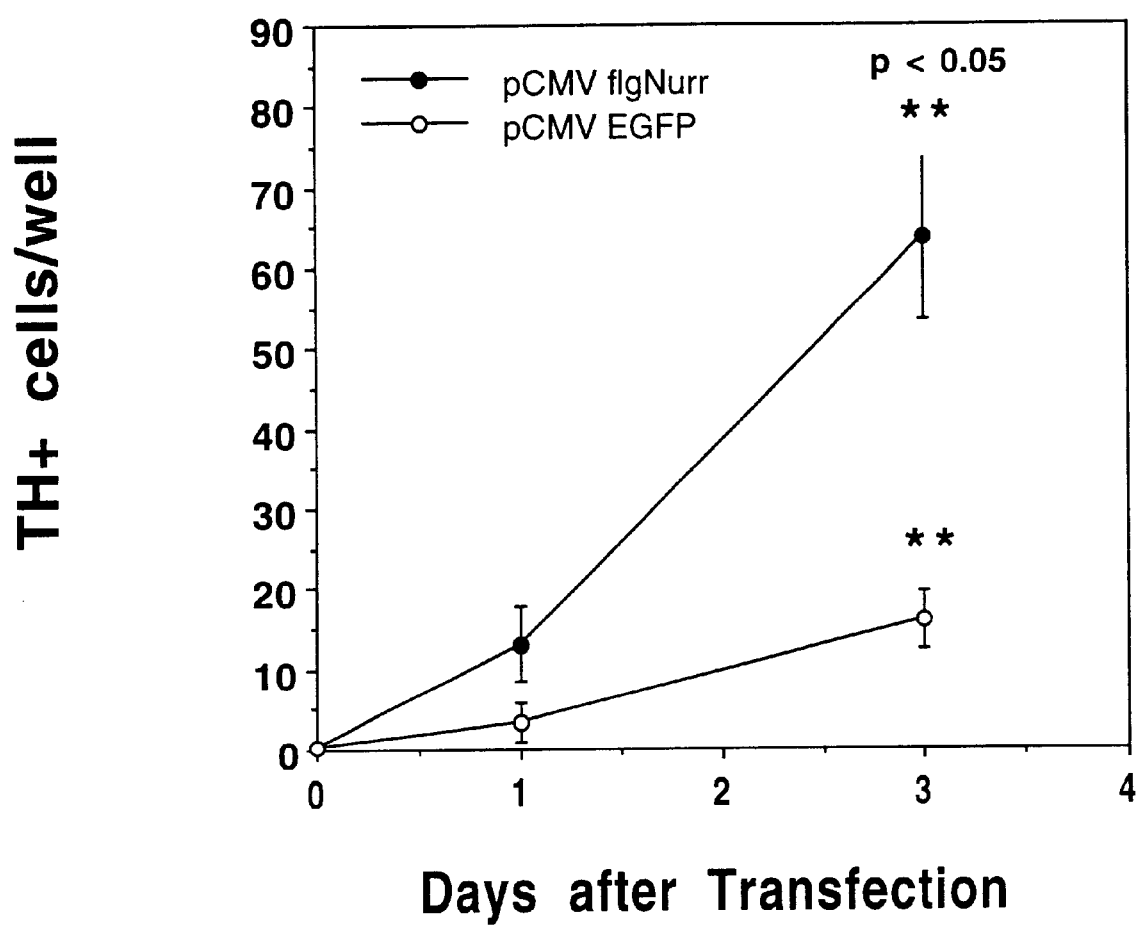
In FIG. 3A, cultures transfected in triplicate with pCMVflgNurr1 (filled circles) or pCMVeGFP (open circles) were stained for TH expression using indirect immunofluorescence. The number of TH+ cells present in each culture was plotted±SEM.
Figure 3B:
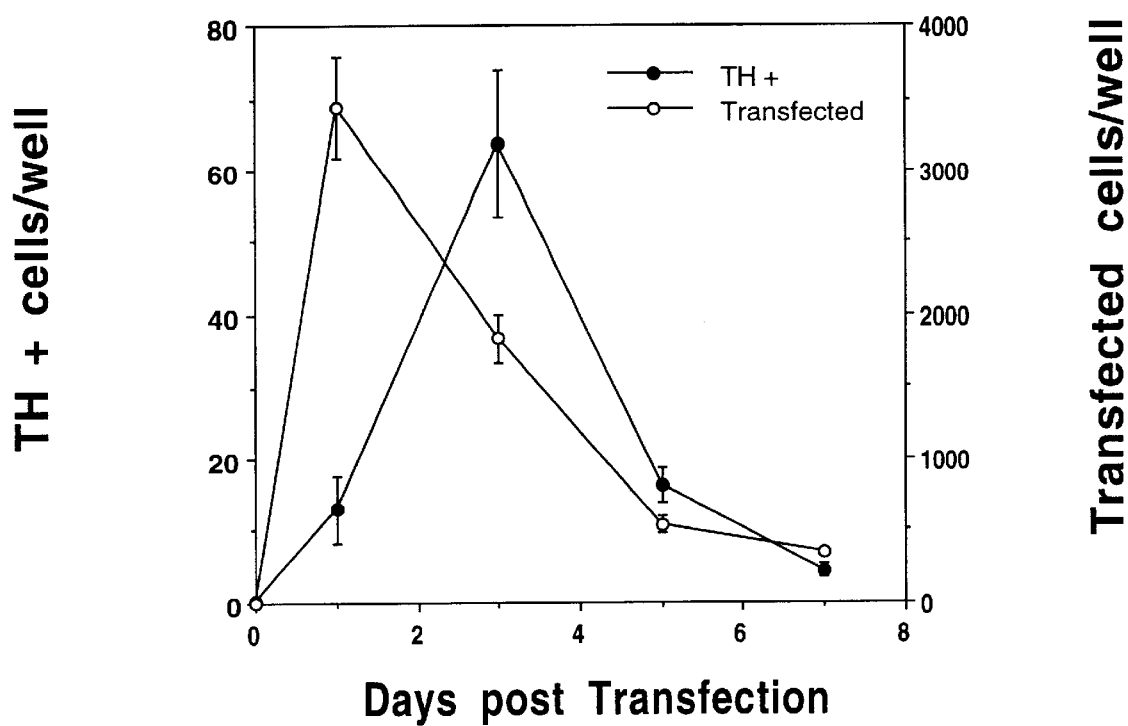
In FIG. 3B, cultures transfected in triplicate with pCMVflgNurr1 were stained for TH and flgNurr1 expression using indirect immunofluorescence. The number of cells expressing the TH (filled circles) or FLAG antigens (open circles) in each culture was plotted±SEM at varying times after transfection. The number of cells expressing the FLAG epitope was quantified using a quadrat or bin of defined size equal to 5% of the total surface area of the well.

The number of TH+ cells in the flgNurr1-transfected cultures rose rapidly after transfection so that by 3 days post-transfection, there was a statistically significant difference ($p<0.05$; n=3) between the number of TH+ cells present in the flgNurr1-transfected cultures and those in the control wells (FIG. 3A). Similar results were obtained in all trials with the relative increase in the number of TH+ cells in cultures transfected with pCMVflgNurr1 ranging from 4 to 45 fold. Interestingly, the peak expression of TH in these cultures lagged by approximately 48 h the peak of flgNurr1 expression. This finding suggests that while a pulse of Nurr1 expression is sufficient to initiate a TH-positive phenotype, sustained Nurr1 expression may be required to maintain that phenotype. In addition, only a fraction of the flgNurr1-transduced cells could be induced to express TH and thus the number of flgNurr1-immunoreactive cells in these cultures far exceeded the number of TH+ cells in these cultures. In a typical experiment, only 3.5% of flgNurr1 positive cells were also immunoreactive for TH at 3 d after transfection.

While the reasons for this discordance are not completely clear, it may be that not all cells within the VM stem cell culture are equally competent to become dopaminergic in response to flgNurr1 expression. For example, some of the transfected cells may have been differentiated glia which are unlikely to retain the capacity to assume a dopaminergic phenotype. Alternately, the level of Nurr1 expression may vary from cell to cell within these cultures so that a cell might express an amount of Nurr1 insufficient to be detectable by immunocytochemistry but yet sufficient to trigger the initiation of the developmental program specifying a dopaminergic phenotype. Finally, the brief expression of Nurr1 produced in these cultures by transient transfection may represent a relatively weak inductive signal that is capable of driving only a few cells to become dopaminergic. It may be that more sustained expression of Nurr1 is required to induce the dopaminergic phenotype in a greater percentage of the VM stem cells. Alternately, cell-type specific promoters may be more efficient than a viral promoter such as CMV in driving Nurr1 gene expression in neural cells to the degree necessary to induce a dopaminergic phenotype.

D. Example 4

Figure 4A:
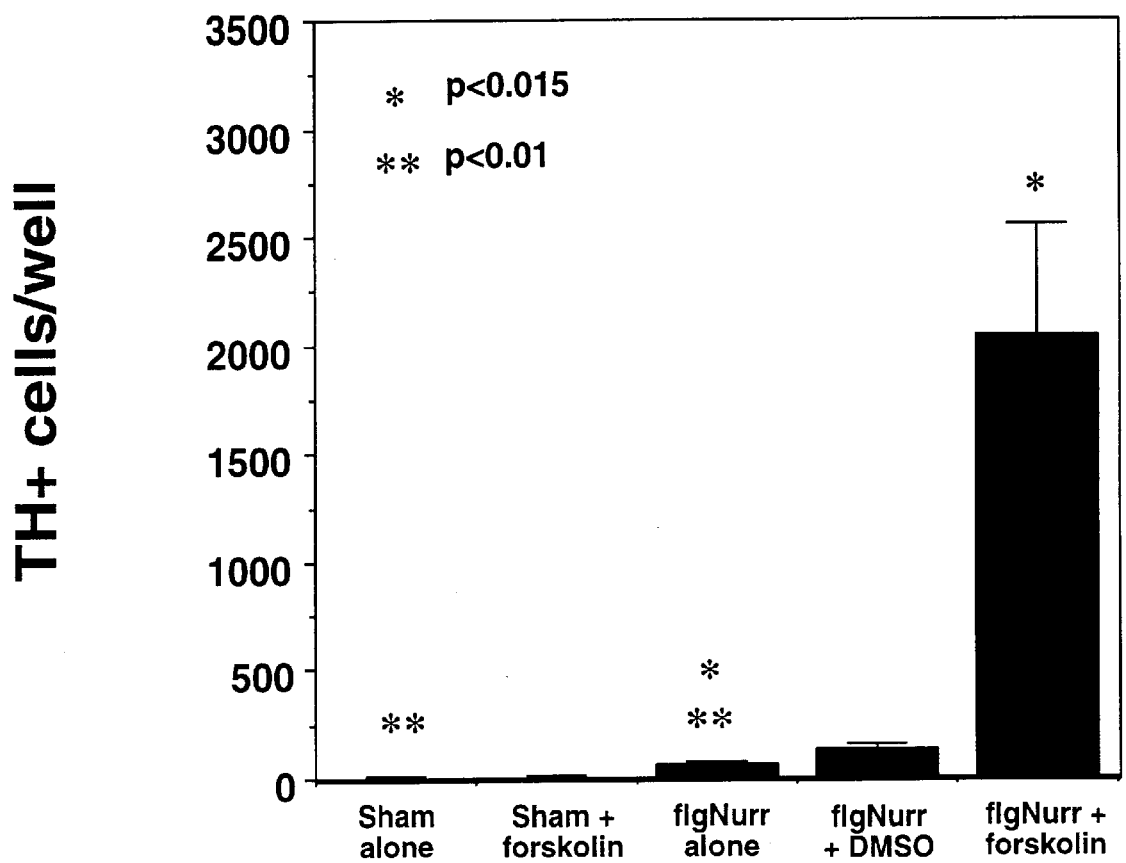
In FIG. 4A, VM stem cell cultures were transfected either with or without pCMVflgNurr1 then treated with DMSO either with or without forskolin. Cultures transfected in triplicate were stained for TH expression using indirect immunofluorescence and the number of TH+ cells present in each culture was plotted±SEM. The number of cells expressing TH was quantified using a quadrat or bin of defined size equal to 5% of the total surface area of the well.

The ability of flgNurr1 to induce a dopaminergic phenotype was significantly potentiated by treating VM stem cell cultures with forskolin, an agonist of protein kinase A (PKA). In these experiments, the cultures were transfected either with or without pCMVflgNurr1 as previously described, but some cultures were treated with 10 $\mu$M forskolin for 3 d after transfection. As shown in FIG. 4A, forskolin treatment of pCMVflgNurr1-transfected cells caused an approximately 50-fold increase in the number of dopaminergic cells over pCMVflgNurr1 transfection alone. This effect of forskolin required transfection with pCMVflgNurr1 since treating sham-transfected cells with forskolin in parallel produced no increase in dopaminergic cells. Similarly, treating pCMVflgNurr1-transfected cells with DMSO, the vehicle in which forskolin was dissolved, also produced no increase in dopaminergic cells when compared to flgNurr1 transfection alone. Thus, the combination of forskolin and Nurr1 expression resulted in a synergistic increase in dopaminergic cells.

While treatment of flgNurr1-transfected cultures with forskolin did produce a slight increase in the number of cells expressing the flgNurr1 transgene, the magnitude ($\approx$3x) of this increase is much smaller than the >30-fold increase in dopaminergic cells produced by the same treatment. Similarly, when we used DAPI, a nonspecific vital dye, to label all cells in transfected cultures either in the presence or absence of forskolin, we found that forskolin treatment had no detectable effect on the total number of cells present in the culture. Using DAPI in conjunction with immunocytochemistry for TH, we found that in cultures transfected with pCMVflgNurr1 in the absence of forskolin, there were 783.3±222.5 cells/mm$^2$ of which 0.35±0.09 or 0.045% were TH+.

Figure 4B:
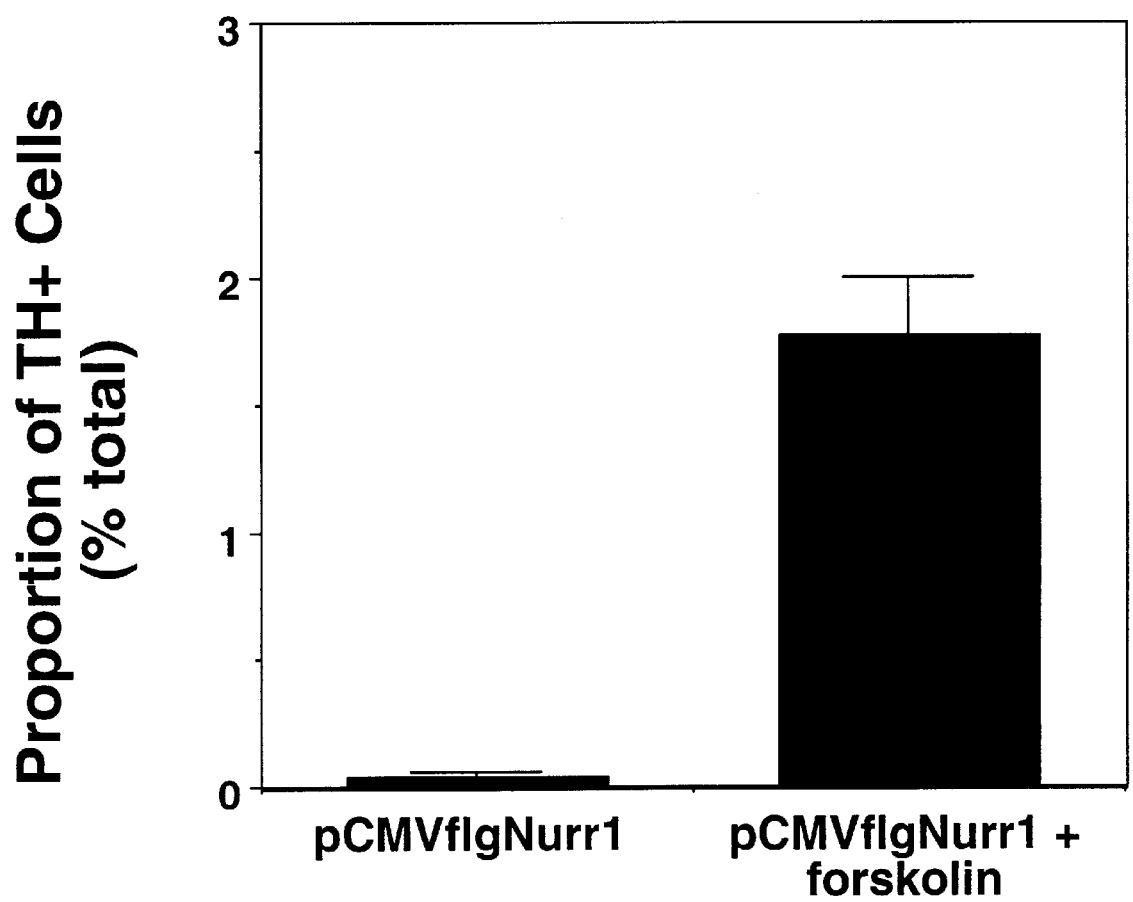
In FIG. 4B, VM stem cell cultures were transfected with pCMVflgNurr1 then treated either with or without forskolin. Cultures transfected in triplicate were stained with the vital dye DAPI and the number of cells present per unit area in each culture was plotted±SEM. Parallel cultures were stained by indirect immunofluorescence for TH. The number of TH+ cells per unit area was quantified and expressed as a percentage±SEM of the total number of cells per unit area.

By contrast, pCMVflgNurr1-transfected cultures treated with forskolin had 911.3±221.3 cells per mm2 of which 16.1±0.52 or 1.77% were TH+. Thus, forskolin treatment appears to enhance specifically the activity of flgNurr1 by increasing not only the total number of TH+ cells in the culture but also their relative abundance (FIG. 4B).

E. Example 5

Figure 5:
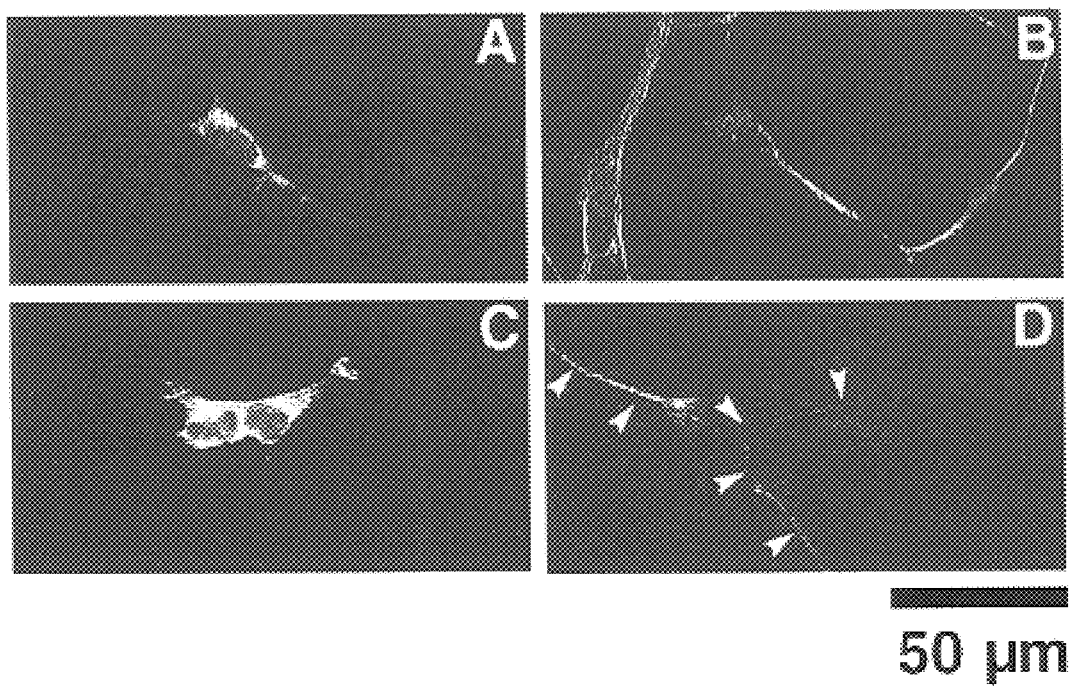
In FIGS. 5(A–D), VM CNS stem cell cultures transfected with pCMVflgNurr1 were doubly immunostained with anti-TH and anti-nestin (5A & 5B) or with anti-TH and anti-MAP2 (5C & 5D). Arrows in 5D indicate a MAP2-positive neurite process that does not coincide with the TH+ cell shown in 5C.

As is evident in FIG. 2, the morphology of TH+ cells in the flgNurr1-transfected cultures was non-neuronal in contrast to the typical TH+ neuronal morphology seen occasionally in the sham- or control-transfected cultures. Consistent with their non-neuronal morphology, the TH+ cells in flgNurr1-transfected cultures co-expressed nestin (FIGS. 5A & 5B) and were negative for MAP2, a marker of mature neurons (FIGS. 5C & 5D).

To determine whether these cells expressed cytochemical markers associated with differentiated neurons, we stained transfected cultures with mAb AP-20 which recognizes the a and b isoforms of MAP2 that are expressed by mature neurons. In these experiments, we found that few TH+ cells in the flgNurr1-transfected cultures co-stained for MAP2a/b (FIGS. 5C & 5D). These observations show that Nurr1 activity is sufficient to induce TH expression in cells that normally do not express this protein.

F. Example 6

To further test this hypothesis, we established CNS stem cells cultures from embryonic rat dorsal midbrain (DM) and lateral ganglionic eminence (LGE) which are both regions that do not normally give rise to TH+ cells either in vitro or in vivo. In Table 1, CNS stem cell cultures from either ventral midbrain (VM), dorsal midbrain (DM) or lateral ganglionic eminence (LGE) were transfected in triplicate with pCMVflgNurr1 then immunostained with anti-TH by indirect immuno-fluorescence. The number of cells in each culture immunopositive for TH was then counted 2 days after transfection. Like VM stem cells cultures, both DM and LGE cultures contained large numbers of TH+ cells after transfection with pCMVflgNurr1 whereas cultures transfected with the control plasmid, pCMVeGFP, contained no TH+ cells (Table 1).

In both DM and LGE cultures, many of the TH+ cells co-stained for flgNurr1 and virtually all had morphologies reminiscent of CNS stem cells rather than neurons. Thus, ectopic expression of Nurr1 induces a dopaminergic phenotype not only in the VM cells which may normally be competent to give rise to TH+ cells, but also in non-VM cells which are usually not competent to generate TH+ cells.

3. UTILITY OF THE INVENTION

A. Use of the Invention in Cell Transplantation Therapy

Through the foregoing set of examples, we have demonstrated that overexpression of Nurr1 can be used to induce a dopaminergic phenotype in a variety of CNS stem cells or other neural precursors from several different brain regions. Although the precise molecular mechanisms by which this effect occurs have not been fully defined, these novel findings nonetheless suggest several potentially significant clinical applications. Most directly, our ability to use Nurr1 expression to increase the dopaminergic cell number could augment existing therapies[22] based on cell transplantation to treat neurological disorders, such as PD, in which dopaminergic function is compromised.

The major pathological feature of PD is the loss of dopaminergic function in the substantia nigra. This pathology can be mimicked in non-human models of the disease by creating pharmacological or surgical lesions of the nigrostriatal dopaminergic pathway. The deficits in motor function that result from such lesions can be largely reversed when cell preparations from the embryonic VM are transplanted into the striatum of the lesioned animals. The critical therapeutic agent in these preparations appears to be dopaminergic neurons since preparations from brain regions lacking dopaminergic neurons provide no therapeutic benefit[6]. Furthermore, embryonic cell preparations from which dopaminergic neurons have been removed by selective neurotoxins also lack efficacy[6]. Finally, the degree of behavioral recovery in animals receiving transplants appears to be related to the number of dopaminergic neurons present in the grafted tissue since transplants in which there is poor survival of dopaminergic neurons fail to induce recovery[6,51].

The use of similar strategies to treat patients with PD has also met with some success[5,8-10,28-30,32,44,55,59,64,65]. Despite these successes, the strategy of using acutely dissociated fetal neural tissue as a source of cells for transplantation has inherent limitations significant enough to render it practically infeasible for widespread application. The major drawback of such an approach is the large number of fetal cells required for transplants to show clinical efficacy. While the exact number of cells used for transplantation varies from trial to trial, cells from approximately 6 aborted fetuses are often used for a single transplantation[41]. Not only does such a large ratio of fetuses to patients raise significant ethical questions, it also creates enormous logistical difficulties in coordinating the collection of tissue or, alternately, of storing collected cells in a manner that preserves their efficacy until transplanted.

For these reasons, much effort has been devoted to finding alternatives to acutely dissociated fetal tissue for use in transplantation. One promising alternative has been to use neural stem cells. The major advantage of these cells is that they can be made to proliferate in a controlled fashion in culture prior to differentiation into neurons. It is thus possible in principle to collect stem cells from a single fetus then expand these cells in vitro to the point where they can be used for a multiplicity of transplantations[22]. However, one limitation of using CNS stem cells as a source of material for transplantation in PD is the relatively low proportion (≈0.1%) of dopaminergic neurons obtained from CNS stem cell cultures[23]. Since the clinical efficacy of transplants is in large part dependent upon the number of dopaminergic cells transplanted, finding a method to increase the proportion of dopaminergic cells in a CNS stem cell culture would have obvious clinical benefits. Indeed, transplantation of cell preparations enriched in dopaminergic cells could have potential applications in disorders of dopaminergic function other than PD including but not limited to neurotoxic injury or disorders of mood and behavior such as addiction and schizophrenia.

Thus, one potential application of the technology described in this application would be to introduce the Nurr1 gene into neural stem cells in order to increase the number of cells displaying a dopaminergic phenotype. The introduction of the Nurr1 gene into cultured CNS stem cells might be coupled with treating these cultures with forskolin or other agonists of PKA activity in order to enhance further the upregulation of the dopaminergic phenotype brought about by Nurr1. Such agonists could include but are not limited to the following:

forskolin;
1,9-dideoxy-forskolin;
6-[[(2-carbethoxyethyl)amino]carbonyl]-forskolin;
6-acetyl-7-deacetyl-forskolin;
6-O-[3'-(piperidino)propionyl]-forskolin hydrochloride;
7-deacetyl-forskolin;
7-deacetyl-6-(N-acetylglycyl)-forskolin;
7-deacetyl-7-[O-(N-methylpiperazino)-g-butyryl]-forskolin, dihydrochloride;
7-deacetyl-7-O-hemisuccinyl-forskolin;
3',5'cyclic monophosphate (cAMP);

8-chloro-cAMP;
8-bromo cAMP;
8-(4-chloropheylthio)-cAMP;
dibutyryl-cAMP;
dioctanoyl-cAMP;
N6-monobutyryl-cAMP;
adenosine 3',5'cyclic monophosphorthioate, Sp-isomer; and
8-bromo-adenosine 3',5'cyclic monophosphorthioate, Sp-isomer.

As shown in Table 1, CNS stem cells both from brain regions that normally contain dopaminergic cells (i.e., VM) and from those that do not (i.e., DM and LGE) can be made to become dopaminergic by forced expression of Nurr1. Indeed, it may turn out that CNS stem cells from regions other than VM are preferable for use in transplantation due to, for example, improved survival or integration into the host. These regions might include but would not be limited to hippocampus, cerebral cortex, striatum, septum, diencephalon, mesencephalon, hindbrain and spinal cord. Thus, the technique of introducing Nurr1 to induce a dopaminergic phenotype, either with or without PKA agonists, could be used not only to increase the number of dopaminergic cells in VM CNS stem cell cultures, but also in CNS stem cell cultures from other brain regions. These regions might include but would not be limited to hippocampus, cerebral cortex, striatum, septum, diencephalon, mesencephalon, hindbrain and spinal cord. It may also be possible to use this technique to induce the dopaminergic phenotype in cell lines either from the CNS or other sources which might then be used for transplantation in Parkinson's patients. Nor would this technology be limited to human cells or human disease. It may be desirable to utilize this technique to induce a dopaminergic phenotype in CNS stem cells derived from non-human sources for use in veterinary medicine. Finally, populations enriched in dopaminergic cells produced by forced expression of Nurr1, treated either with or without PKA agonists, might prove useful as a platform for discovering drugs capable of regulating the survival, proliferation or genesis of dopaminergic cells.

While the transient transfection method used in this application is one possible method to introduce the Nurr1 gene into cells, the invention does not require this specific method. Indeed, any other method(s) for introducing a gene into cells might prove to be optimal. These methods would include but not be limited to incorporating the Nurr1 gene into a retrovirus, an adenovirus, an adeno-associated virus or a lentivirus or introducing the gene into cells by electroporation, biolistics, direct injection or virus-augmented transfection. Nor would the potential uses of this technology be limited to the gene for epitope-tagged mouse Nurr1 as described in this application. An untagged gene from mouse, human or any other species could also be used as could DNA constructs coding for biologically active fragments of Nurr1 or of Nurr1 homologues such as Nur77. Finally, Nurr1 expression need not be driven by the CMV promoter, as described in this application. We envision potential uses of this technology in which the Nurr1 gene is driven by other viral promoters or by promoters for endogenous mammalian genes which yield either general or cell-type specific expression. Furthermore, we envision potential uses in which the gene for Nurr1 is driven by inducible promoters, including but not limited to those that are controlled by antibodies, temperature, heavy metals or hormones.

B. Use of the Invention for Drug Screening

The potential applications of the technology described in this application extend beyond its use to augment cell transplantation therapy. From the experiments described in this application as well as from the phenotype of the Nurr1 null mouse, it appears that there is a direct relationship between levels of Nurr1 expression and the prevalence of the dopaminergic phenotype. Thus, in the absence of Nurr1, there are no dopaminergic neurons in the substantia nigra at the time of birth. Conversely, overexpression of Nurr1 results in an increased number of dopaminergic cells in vitro. These findings imply that the level of Nurr1 expression is intimately related to the prevalence of the dopaminergic phenotype. Thus, pharmacological or growth factor treatments that upregulate Nurr1 would be expected to increase the prevalence of the dopaminergic phenotype. From this it follows that one valuable way to determine if a particular treatment is able to promote the dopaminergic phenotype would be to ask whether that condition or treatment is capable of upregulating Nurr1.

We thus envision a drug screening system in which potentially bioactive substances are screened for their ability to affect the expression levels of Nurr1 as a means to determine whether these substances are likely to have the ability to increase the prevalence of the dopaminergic phenotype. Formally, such an assay would consist of exposing a cells to a particular culture condition or potentially bioactive substance, then monitoring whether that exposure affected the level of Nurr1 expression within a cell or cell population. This fairly simple formal structure permits great versatility in its practical application as numerous of its parameters can be adjusted without altering its fundamental nature. For example, the cell type used in an assay of this sort could be a CNS stem cell from VM, DM, LGE or other brain region or the cell type used could be from an established cell line of neural or other origin. Alternately, the cell type employed in the assay could be a neuron acutely dissociated from tissue or a neuron derived from the in vitro differentiation of CNS stem cells or CNS stem cell-derived cell line. Similarly, culture conditions to be assayed could include but would not be limited to culturing the cells to be assayed at different densities, in different media, on different substrates or in the presence of other cell populations.

An equally wide variety of potentially bioactive substances could be assayed for their affect on the dopaminergic phenotype in this type of assay. These would include but not be limited to extracts from tissues or cells, conditioned media from primary cells or cell lines, polypeptides whether naturally occurring or recombinant, DNA or RNA molecules and non-protein molecules whether naturally occurring or chemically synthesized. Nurr1 expression could be monitored by a wide variety of techniques, including measuring the levels of Nurr1 protein with biochemical and/or immunological methods or measuring Nurr1 mRNA levels by hybridization and/or PCR or measuring the level of Nurr1 gene expression using a recombinant promoter/reporter gene expression system. This latter approach would involve expressing within the cells used for drug screening a DNA construct comprising such cis regulatory elements as are needed to regulate the endogenous expression of Nurr1 operably linked to a reporter gene(s). In a construct of this type, the Nurr1 regulatory elements would modulate the transcription of the reporter genes so that the expression of the reporter would faithfully indicate the level of Nurr1 transcription. Candidate reporter genes would include but would not be limited to luciferase, bioluminescent proteins, chloramphenicol acetyltransferase, β-galactosidase, β-lactamase or other antibiotic resistance gene, neurotrophins or cytokines.

Indeed, since Nurr1 itself regulates gene expression by binding to a characterized DNA sequence $(AAAGGTCA)^{56}$ known as the Nurr1 response element, we can use the approach just described to create cells for use in drug screening capable of measuring the expression level not only of Nurr1 but also of genes regulated by Nurr1. To do so, a reporter gene would be linked to a promoter containing the Nurr1 response element. Cells incorporating this promoter-reporter construct would then be exposed to potentially bioactive substances.

Any substance capable of activating Nurr1 would cause Nurr1 to bind to its response element and thus drive the expression of the reporter gene. Through this approach, it would be possible to monitor the specific transcription-promoting activity of Nurr1 either instead of or in conjunction with measuring the expression levels of the Nurr1 gene itself. Using levels of Nurr1 expression or activity as a surrogate marker for the dopaminergic phenotype in this manner offers several advantages over current methods for determining whether a particular culture condition or substance affects the decision of a cell to adopt the dopaminergic phenotype.

The most commonly used current method for monitoring dopaminergic phenotype relies on immunocytochemical methods to determine whether a particular cell expresses TH. This type of assay, though informative, is laborious and time consuming. Using levels of Nurr1 expression or activity as an indirect, though faithful, marker for the dopaminergic phenotype would allow for more rapid and high-throughput methods for determining whether particular treatments affect this phenotype.

Example 7

More specifically, we have shown that using transfection to artificially raise Nurr1 expression levels causes dopaminergic cells to be generated from neural precursors. From this it follows that a substance or substances—as yet unidentified—capable of increasing Nurr1 expression or activity pharmacologically will likely have this same valuable effect.

The following is a first example of a strategy to identify such substances (see FIG. 6):

a) Culture stem cells or other cells endogenously expressing Nurr1.

b) Expose the cultured cells to substances to be assayed for their ability to raise the level of Nurr1 expression or activity. These substances could be proteins or other large or small molecules whether artificially synthesized or derived from natural products.

c) Determine whether any of these substances cause an increase in the expression of Nurr1 at the level of the protein or of the RNA.

Example 8

The following is a second example of a strategy to identify substances that increase Nurr1 expression (see FIG. 7):

a) First, introduce into stem cells or other cell types a construct comprising the Nurr1 promoter linked to a reporter gene. Candidate reporter genes would include but would not be limited to luciferase, bioluminescent proteins, chloramphenicol acetyltransferase, β-galactosidase, β-lactamase or other antibiotic resistance gene, neurotrophins or cytokines.

Figure 8:
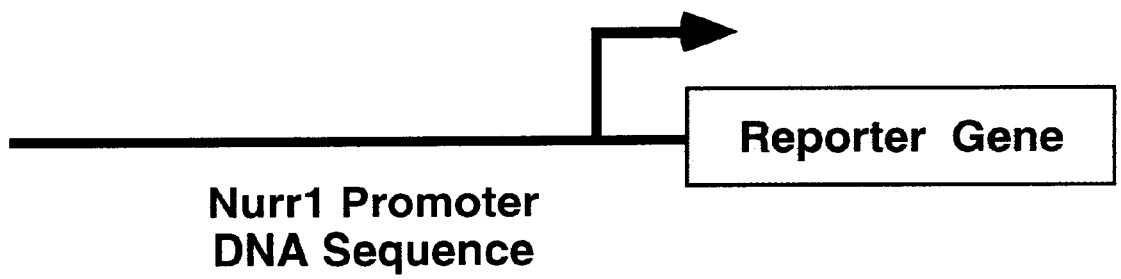
In FIG. 8, a schematic representation of a DNA construct in which the expression of a reporter gene is regulated by the Nurr1 promoter is shown.

Using the Nurr1 promoter to control the expression of a reporter gene means that any substance that is capable of increasing Nurr1 expression will now increase the expression of the reporter gene in addition to simply increasing the expression of endogenous Nurr1 (see FIG. 8). The reporter will have been chosen because there exists some very simple means to measure its expression level, e.g., emitted light in the case of GFP.

b) Culture cells expressing a construct of the type described above.

c) Expose the cultured cells to substances of potential therapeutic value.

d) Determine whether any of the substances cause an increase in the expression of the reporter gene by examining the level of its protein, RNA, biological activity or other measure.

Example 9

The following is a third example of a strategy to identify substances that increase Nurr1 expression (see FIG. 9):

a) Introduce into stem cells or other cells a construct comprising the Nurr1 response element linked to a reporter gene. The proviso here is that the cells selected must express Nurr1, either endogenously or due to the artificial introduction of the Nurr1 gene.

Figure 10:
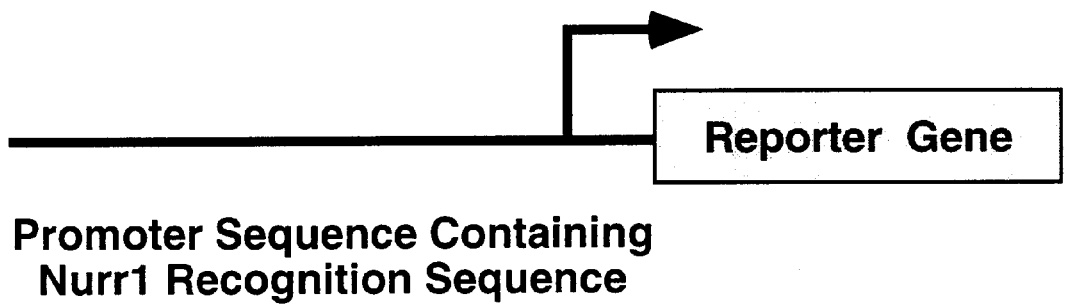
In FIG. 10, a schematic representation of a DNA construct in which the expression of a reporter gene is regulated by a DNA sequence incorporating the Nurr1 recognition sequence (AAAGGTCA) is shown.

The Nurr1 response element (AAAGGTCA) is the DNA sequence to which Nurr1 specifically binds. Once Nurr1 binds this DNA sequence, it can regulate the expression of genes downstream of this element. Cells expressing such a construct will exhibit an increased rate of reporter gene transcription in the presence of substances that can increase the ability of Nurr1 to stimulate the transcription of genes downstream of the AAAGGTCA sequence (see FIG. 10).

b) Culture cells expressing a construct of the type described above.

c) Expose the cultured cells to substances of potential therapeutic value.

d) Determine whether any of these substances cause an increase in the expression of the reporter gene by examining the level of its protein, RNA, biological activity or other measure.

C. Use of the Invention for Gene Discovery

In addition to the uses described above, the technology described in this application could be utilized as a means to discover novel genes of potential therapeutic value that are part of the signalling cascade by which Nurr1 activity leads to the assumption of a dopaminergic phenotype. Many nuclear receptors regulate sets of genes involved in a particular physiological pathway[13] and Nurr1 activity likely upregulates more than just the TH gene. Rather, Nurr1 activation probably leads to changes in the expression level of several downstream genes involved in specifying the dopaminergic phenotype. While many such genes may well have previously been identified or characterized, it seems plausible some genes regulated by Nurr1 may be as yet unidentified. Even if this is not the case and all the genes upregulated by Nurr1 have indeed been identified, their function in specifying a dopaminergic phenotype may not have been previously recognized. By participating in the process through which the dopaminergic phenotype is specified, these genes may represent unrealized targets for therapies designed to alleviate a loss in dopaminergic function.

To identify such genes, we envision establishing cell populations expressing Nurr1 constructs in which the activity and/or expression level of Nurr1 is regulated in a controllable fashion. One means to accomplish this goal would be to place the Nurr1 gene downstream of an inducible promoter and then introduce this construct into a suitable host cell. Exposing the cells to the agent capable of inducing promoter activity would therefore increase the transcription of Nurr1. Another non-limiting possibility would be to introduce into host cells a DNA construct coding for a chimeric Nurr1 protein in which the transactivating, DNA-binding domain of Nurr1 is fused to the ligand-binding domain of some other nuclear receptor, such as the estrogen receptor. Estrogen could then be used to activate the ligand-binding (estrogen receptor) domain of the chimera and thus cause the DNA-binding (Nurr1) domain to bind its specific DNA recognition sequence and thus activate the transcription of genes normally regulated by Nurr1. Once constructs such as or similar to those just described are introduced into cells, we would be able to increase Nurr1 activity at will in these cells to initiate the signalling pathway leading to a dopaminergic phenotype. It would then be possible to compare numerous physiological parameters in Nurr1-stimulated versus quiescent cells. Such parameters would include but not be limited to the complement of genes expressed by stimulated and unstimulated cells, the post-translational modifications of known proteins, the functioning of ion channels or the intracellular localization of particular molecules. This broad range of comparison would admit an equally broad range of techniques comparison including but not limited to subtractive hybridization, differential display, SAGE, biochemical fractionation, electrophysiology or cytochemical techniques. The choice of suitable cell types to be subjected to such a gene discovery program would be equally wide-ranging and would include but not be limited to primary CNS stem cells, CNS stem cell-derived cell lines, primary cells derived from neural or other sources or established cell lines.

Example 10

More specifically, we have shown that Nurr1 regulates the expression of at least one gene, tyrosine hydroxylase, in the signalling pathway by which a cell acquires a dopaminergic phenotype. It seems reasonable to suppose that TH is not the only gene in this pathway regulated by Nurr1. Any additional genes regulated by Nurr1 are likely to be important in generating dopaminergic cells and are thus potentially clinically significant. To identify such genes, we compare the complement of genes expressed by cells in which Nurr1 is active to that of cells in which it is not.

Figure 11:
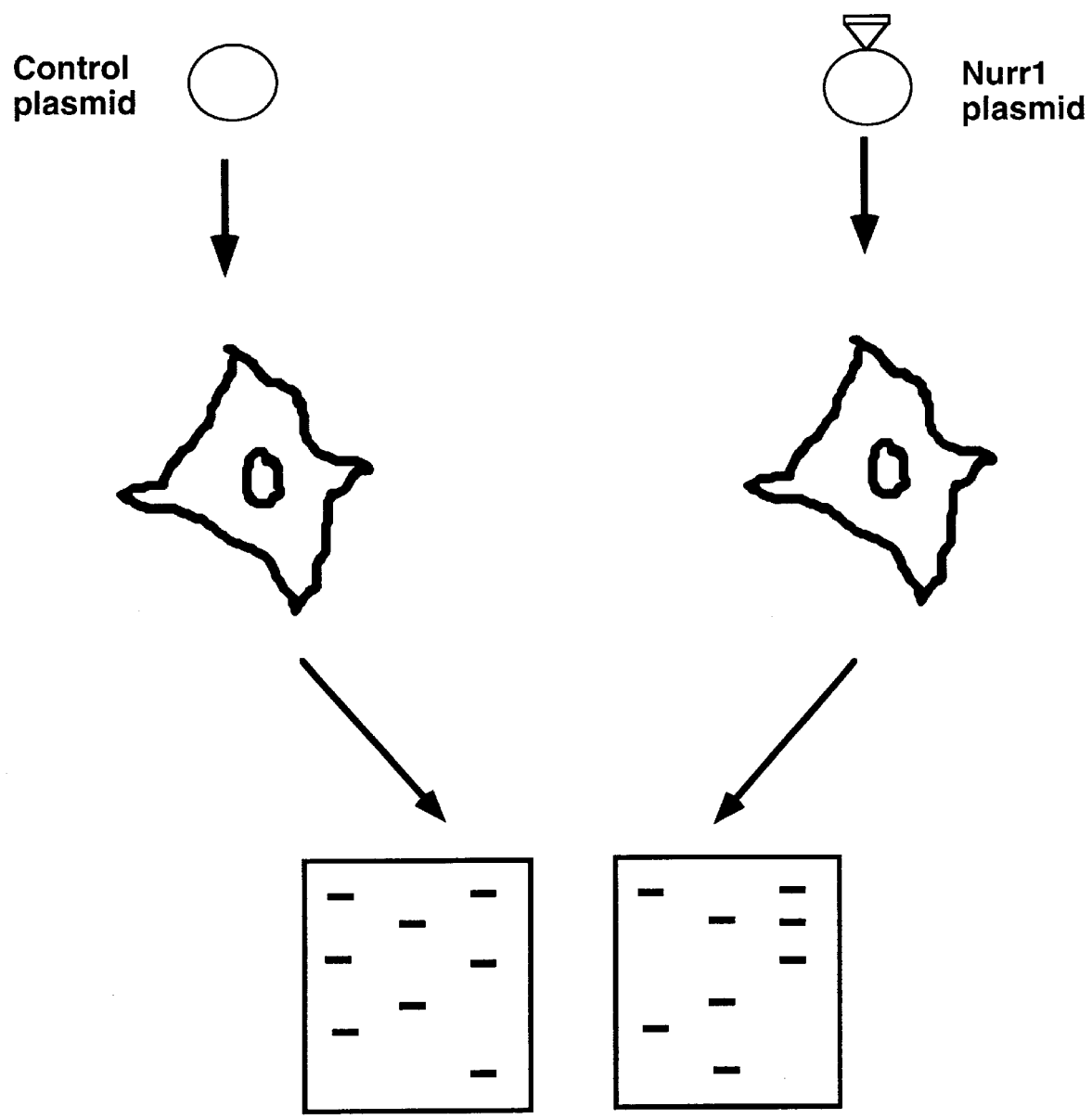
In FIG. 11, a first example of a strategy to identify genes in the signalling pathway by which a cell acquires a dopaminergic phenotype is shown.
Figure 13:
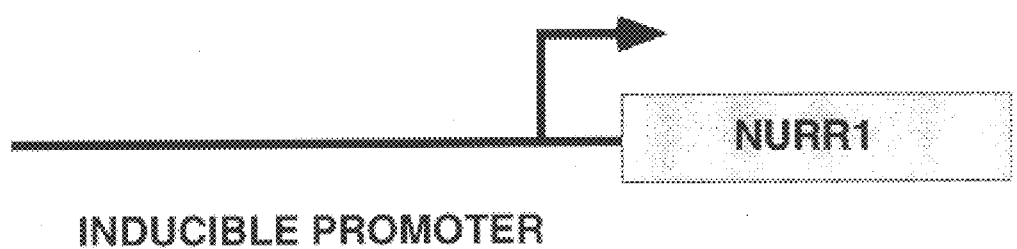
In FIG. 13, a schematic representation of a DNA construct in which the expression of Nurr1 is regulated by an inducible promoter is shown.

The following is a first example of a strategy to identify genes in the signalling pathway by which a cell acquires a dopaminergic phenotype (see FIG. 11).

a) Introduce the Nurr1 gene into cultures of stem cells or other cells.

b) Examine the genes expressed in the cultures into which Nurr1 has been introduced relative to those expressed in cultures in which the Nurr1 gene has not been introduced.

The examination of gene expression would include but not be limited to the complement of genes expressed by stimulated and unstimulated cells, the post-translational modifications of known proteins, the functioning of ion channels or the intracellular localization of particular molecules. As above, this broad range of comparison would admit an equally broad range of techniques comparison including but not limited to subtractive hybridization, differential display, SAGE, biochemical fractionation, electrophysiology or cytochemical techniques.

c) Identify genes in the signalling pathway by which a cell acquires a dopaminergic phenotype.

Example 11

The following is a second example of a strategy to identify genes in the signalling pathway by which a cell acquires a dopaminergic phenotype (see FIG. 12).

a) Introduce into cultured stem cells or other cells a construct comprising the Nurr1 coding sequence under the control of an inducible promoter, e.g., the tetracycline-inducible promoter.

b) Expose the cells expressing such a construct to the substance capable of regulating the expression of genes under the control of the inducible promoter, e.g., tetracycline, or to an inactive control substance.

c) Compare the complement of genes expressed in the cells that have been treated with the inducing agent to the complement of genes expressed by the cells treated with the inactive control.

d) Identify genes in the signalling pathway by which a cell acquires a dopaminergic phenotype.

Example 12

Figure 14:
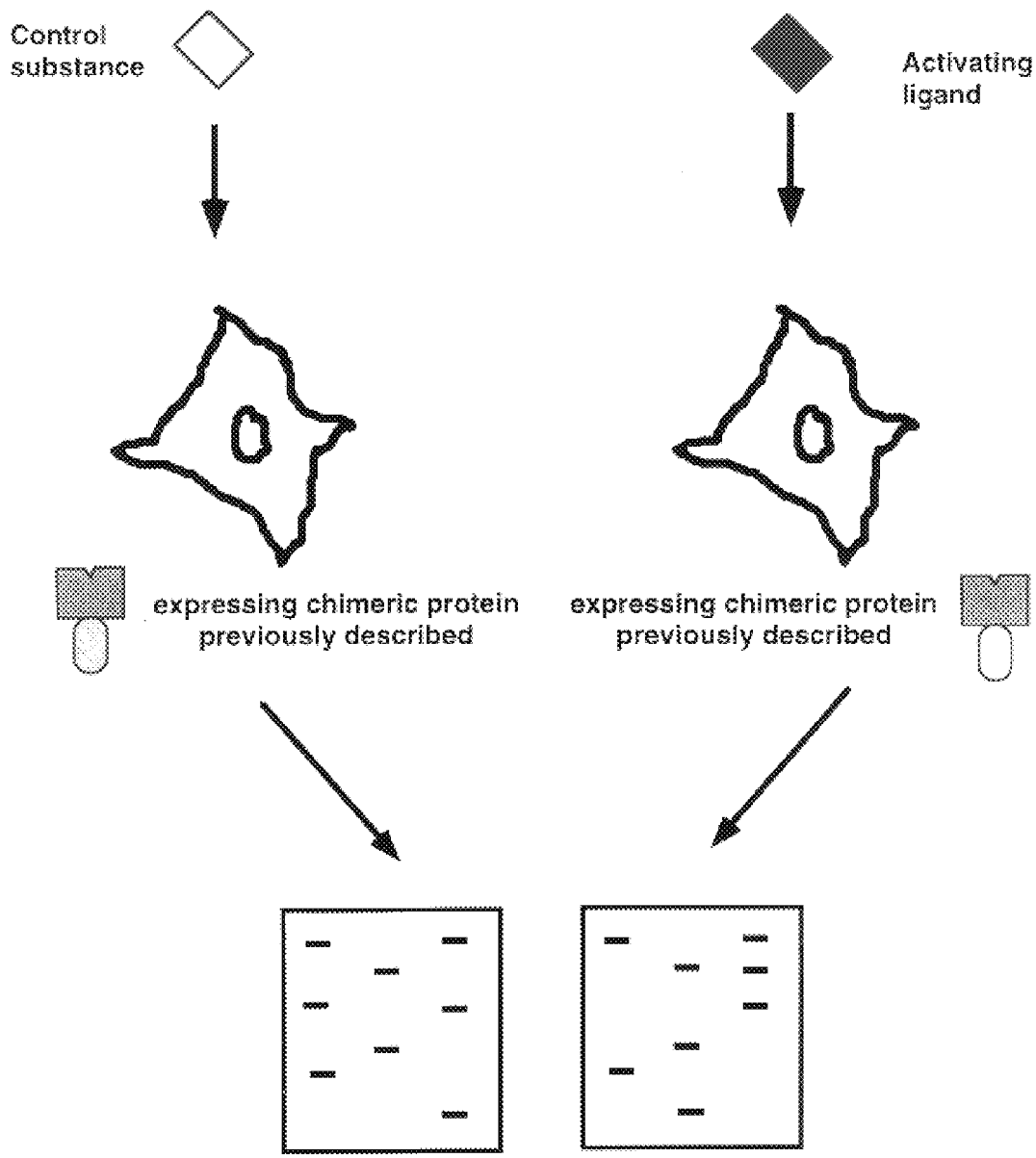
In FIG. 14, a third example of a strategy to identify genes in the signalling pathway by which a cell acquires a dopaminergic phenotype is shown.
Figure 15:
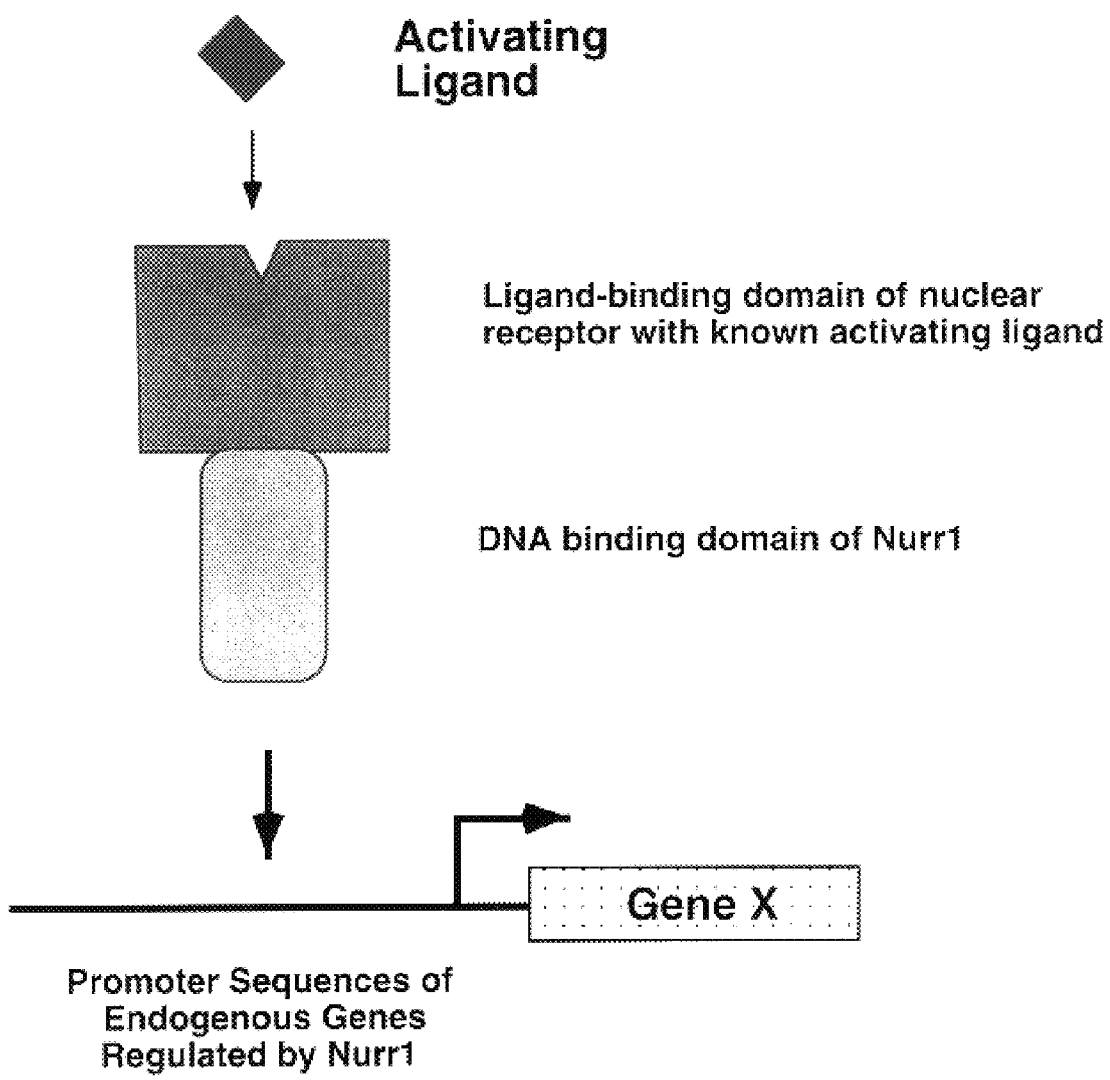
In FIG. 15, a schematic representation of a DNA construct encoding a chimeric protein consisting of the ligand-binding domain of a nuclear receptor with a known ligand and the DNA-binding domain of Nurr1 is shown.

The following is a third example of a strategy to identify genes in the signalling pathway by which a cell acquires a dopaminergic phenotype (see FIG. 14).

a) Introduce into cultured stem cells or other cells a construct coding for a chimeric protein in which the DNA binding domain of Nurr1 is fused to the ligand-binding domain of a nuclear receptor with a known activating ligand, e.g., the estrogen receptor (see FIG. 15).

b) Expose the cells to the activating ligand of the chimeric protein, e.g., estrogen, or to an inactive control substance.

c) Compare the complement of genes expressed in the cells that have been treated with the activating ligand to the complement of genes expressed by the cells treated with the inactive control substance.

d) Identify genes in the signalling pathway by which a cell acquires a dopaminergic phenotype.

Example 13

The following is a fourth example of a strategy to identify genes in the signalling pathway by which a cell acquires a dopaminergic phenotype.

a) Culture stem cells or other cells that express Nurr1, either endogenously or due to the artificial introduction of the Nurr1 gene.

b) Expose the cells to substances capable of upregulating Nurr1 expression or activity. Such substances are as yet unidentified but may be identified via drug discovery assays of the types described above.

c) Examine the genes expressed in cells exposed to this Nurr1-regulating substance compared to cell not exposed to the substance.

d) Identify genes in the signalling pathway by which a cell acquires a dopaminergic phenotype.

D. Use of the Invention for Gene Therapy or Diagnostics

Finally, manipulation of Nurr1 expression may be of value in directly treating neurological disease. One possibility in this regard is that the initial cause of motor dysfunction in PD may not be due to the death of dopaminergic neurons in the substantia nigra, but rather from a loss of their function. Indeed there is some recent evidence to support the notion that dopaminergic neurons persist in the substantia nigra of PD patients—albeit in a functionally compromised state. Ptx-3, a gene that is an early marker for dopaminergic neurons remains expressed in the substantia nigra of PD patients though at reduced levels compared to healthy controls, despite the massive loss of TH expression and a concomitant loss in dopaminergic function shown by these patients[58]. Such a finding raises the possibility that the cells which would normally secrete dopamine remain present in the substantia nigra of PD patients, but for some reason cease to express their dopaminergic phenotype. Since Nurr1 function is critical for the assumption of a dopaminergic phenotype, it is possible that an increase in Nurr1 function would boost the ability of these cells to express the dopaminergic phenotype and would thus restore dopaminergic function.

If indeed PD results even in part from a failure of nigral neurons to express the dopaminergic phenotype rather than from the physical degeneration of these cells, then one possible therapy for this disorder would be to augment Nurr1 function in these cells as a means to restore the dopaminergic phenotype. Such augmentation might be accomplished pharmacologically by administering substances capable of upregulating Nurr1 or its transcriptional activity. Alternately, Nurr1 augmentation might be effected by boosting Nurr1 expression in PD patients via gene therapy. In such an approach, the Nurr1 gene or fragments thereof would be introduced directly into cells in a PD-affected patient using any of several methods of in vivo gene delivery.

If indeed the etiology underlying PD is a deficiency in dopaminergic function rather than a loss of dopaminergic cells, then this deficit might manifest itself prior to the onset of clinical symptoms of PD. In fact it is possible that in some patients, a loss of dopaminergic function may result from structural or functional abnormalities is Nurr1 itself. If so, then such patients might show abnormalities in Nurr1 evident at the level of the protein, of the mRNA or of the gene. We envision screening for such abnormalities as a means to provide early, perhaps presymptomatic, detection of PD. Alternately, detection of abnormalities in Nurr1 may serve as a biochemical confirmation of a diagnosis of PD made initially after a neurological examination. Abnormalities in the Nurr1 protein could be detected by biochemical or immunological methods while hybridization or PCR-based methods could be used to screen for abnormalities in the structure of the Nurr1 mRNA or gene. These techniques could be applied to brain biopsies, cerebrospinal fluid, blood, saliva, urine or other bodily fluid or tissue.

One consequence of the degeneration of dopaminergic cells in the substantia nigra might be the liberation of Nurr1 protein from the nuclei of these cells. As a result of this degeneration, Nurr1 may accumulate in the cerebrospinal fluid, blood or brain tissue of affected patients. The accumulation of Nurr1 in these or other bodily compartments may therefore serve as an early presymptomatic marker for the onset of PD. If so, a means to detect such a marker would have enormous clinical significance by allowing for early intervention in the progress of the disease. Alternately, accumulation of Nurr1 may serve as a biochemical confirmation of a diagnosis of PD made initially after a neurological examination. The techniques usable in such a screen would include but would not be limited to immunological or biochemical methods of Nurr1 detection.

Example 14

More specifically, we have shown in vitro that Nurr1 expression can cause the generation of a dopaminergic phenotype in neural cells. If the same is true in vivo, as seems likely, then introducing Nurr1 into neural cells in the brain may increase the number of dopaminergic cells in the brains of patients in need thereof.

The following is a first example of a strategy for in vivo therapy.

Introduce the Nurr1 gene into the brain of a patient experiencing compromised dopaminergic function. Any of the various methods of in vivo gene delivery may be used.

Example 15

The following is a second example of a strategy for in vivo therapy.

Treat a patient experiencing compromised dopaminergic function with substances capable of upregulating Nurr1 expression or activity. Such substances are as yet unidentified but may be identified via drug discovery assays of the types described above.

E. Diagnostics

Since, as we have shown, Nurr1 is centrally involved in regulating dopaminergic function, it may be that a loss of dopaminergic function in patients is due to structural or functional abnormalities in Nurr1. We propose to examine Nurr1 structure and/or function in patients suspected to have compromised dopaminergic function. This test of Nurr1 structure or function could be performed at the level of the protein, the mRNA message or the DNA.

4. REFERENCES

The following scientific articles and patents have been cited throughout this application:

1. Brown, J. R., B. Ye, R. T. Bronson, P. Dikkes, and M. E. Greenberg. (1996) A defect in nurturing in mice lacking the immediate early gene fosB. *Cell* 86: 297–309.
2. Castillo, S. O., J. S. Baffi, M. Palkovits, G. D. S., I. J. Kopin, J. Witta, M. A. Magnuson, and V. M. Nikodem. (1998) Dopamine biosynthesis is selectively abolished in substantia nigra/ventral tegmental area but not in hypothalamic neurons in mice with targeted disruption of the Nurr1 gene. *Mol. Cell. Neurosci.* 11: 36–46.
3. Castillo, S. O., Q. Xiao, M. S. Lyu, C. A. Kozak, and V. M. Nikodem. (1997) Organization, sequence, chromosomal localization, and promoter identification of the mouse orphan nuclear receptor Nurr1 gene. *Genomics* 41: 250–257.
4. Chang, C., J. Kokontis, S. S. Liao, and Y. Chang. (1989) Isolation and characterization of human TR3 receptor: a member of steroid receptor superfamily. *J Steroid Biochem* 34: 391–395.
5. Defer, G. L., C. Geny, F. Ricolfi, G. Fenelon, J. C. Monfort, P. Remy, G. Villafane, R. Jeny, Y. Samson, Y. Keravel, A. Gaston, J. D. Degos, M. Peschanski, P. Cesaro, and J. P. Nguyen. (1996) Long-term outcome of unilaterally transplanted parkinsonian patients. I. Clinical approach. *Brain* 119: 41–50.
6. Dunnett, S. B., T. D. Hernandez, A. Summerfield, G. H. Jones, and G. Arbuthnott. (1988) Graft-derived recovery from 6-OHDA lesions: specificity of ventral mesencephalic graft tissues. *Exp Brain Res* 71: 411–424.
7. Escriva, H. R. Safi, C. Hanni, M. C. Langlois, P. Saumitou-Laprade, D. Stehelin, A. Capron, R. Pierce, and V. Laudet. (1997) Ligand binding was acquired during evolution of nuclear receptors. *Proc Natl Acad Sci U S A* 94: 6803–6808.
8. Freed, C. R., R. E. Breeze, N. L. Rosenberg, and S. A. Schneck. (1993) Embryonic dopamine cell implants as a treatment for the second phase of Parkinson's disease. Replacing failed nerve terminals. *Adv Neurol* 60: 721–728.

9. Freed, C. R., R. E. Breeze, N. L. Rosenberg, S. A. Schneck, T. H. Wells, J. N. Barrett, S. T. Grafton, S. C. Huang, D. Eidelberg, and D. A. Rottenberg. (1990) Transplantation of human fetal dopamine cells for Parkinson's disease. Results at 1 year. *Arch Neurol* 47: 505–512.
10. Freeman, T. B., C. W. Olanow, R. A. Hauser, G. M. Nauert, D. A. Smith, C. V. Borlongan, P. R. Sanberg, D. A. Holt, J. B. Kordower, F. J. Vingerhoets, and et al. (1995) Bilateral fetal nigral transplantation into the postcommissural putamen in Parkinson's disease. *Ann Neurol* 38: 379–388.
11. Freund, C. L., C. Y. Gregory-Evans, T. Furukawa, M. Papaioannou, J. Looser, L. Ploder, J. Bellingham, D. Ng, J. A. Herbrick, A. Duncan, S. W. Scherer, L. C. Tsui, A. Loutradis-Anagnostou, S. G. Jacobson, C. L. Cepko, S. S. Bhattacharya, and R. R. McInnes. (1997) Cone-rod dystrophy due to mutations in a novel photoreceptor-specific homeobox gene (CRX) essential for maintenance of the photoreceptor. *Cell* 91: 543–553.
12. Furukawa, T., E. M. Morrow, and C. L. Cepko. (1997) Crx, a novel otx-like homeobox gene, shows photoreceptor-specific expression and regulates photoreceptor differentiation. *Cell* 91: 531–541.
13. Glass, C. K. (1994) Differential recognition of target genes by nuclear receptor monomers, dimers, and heterodimers. *Endocr Rev* 15: 391–407.
14. Harlow, E., and D. Lane. Antibodies: *A Laboratory Manual*: Cold Spring Harbor Laboratory, N.Y., 1988.
15. Hazel, T. G., D. Nathans, and L. F. Lau. (1988) A gene inducible by serum growth factors encodes a member of the steroid and thyroid hormone receptor superfamily. *Proc Natl Acad Sci U S A* 85: 8444–8448.
16. Hillier, L., M. Allen, L. Bowles, T. Dubuque, G. Geisel, S. Jost, T. Kucaba, M. Lacy, N. Le, G. Lennon, M. Marra, J. Martin, B. Moore, K. Schellenberg, M. Steptoe, F. Tan, B. Theising, Y. White, T. Wylie, R. Waterston, and R. Wilson (1997) Genbank submission: Soares ovary tumor NbHOT Homo sapiens cDNA clone 756580. Accession No.: AA481687.
17. Hillier, L., M. Allen, L. Bowles, T. Dubuque, G. Geisel, S. Jost, T. Kucaba, M. Lacy, N. Le, G. Lennon, M. Marra, J. Martin, B. Moore, K. Schellenberg, M. Steptoe, F. Tan, B. Theising, Y. White, T. Wylie, R. Waterston, and R. Wilson (1997) Genbank submission: Soares ovary tumor NbHOT Homo sapiens cDNA clone 770652. Accession No.: AA454469.
18. Hillier, L., M. Allen, L. Bowles, T. Dubuque, G. Geisel, S. Jost, T. Kucaba, M. Lacy, N. Le, G. Lennon, M. Marra, J. Martin, B. Moore, K. Schellenberg, M. Steptoe, F. Tan, B. Theising, Y. White, T. Wylie, R. Waterston, and R. Wilson (1997) Genbank submission: Soares_total_fetus_Nb2HF8_9w Homo sapiens cDNA clone 796194. Accession No.: AA461422.
19. Honkaniemi, J., S. M. Sagar, I. Pyykonen, K. J. Hicks, and F. R. Sharp. (1995) Focal brain injury induces multiple immediate early genes encoding zinc finger transcription factors. *Brain Res Mol Brain Res* 28: 157–163.
20. Hynes, M., J. A. Porter, C. Chiang, D. Chang, M. Tessier-Lavigne, P. A. Beachy, and A. Rosenthal. (1995) Induction of midbrain dopaminergic neurons by Sonic hedgehog. *Neuron* 15: 35–44.
21. Jessell, T. M., and J. Dodd. (1990) Floor plate-derived signals and the control of neural cell pattern in vertebrates. *Harvey Lect* 86: 87–128.
22. Johe, K. K. (1998). Isolation propagation and directed differentiation of stem cells from embryonic and adult central nervous system of mammals. U.S. Pat. No. 5,753,506.
23. Johe, K. K., T. G. Hazel, T. Muller, M. M. Dugich-Djordjevic, and R. D. McKay. (1996) Single factors direct the differentiation of stem cells from the fetal and adult central nervous system. *Genes Dev* 10: 3129–3140.
24. Kalir, H. H., and C. Mytilineou. (1991) Ascorbic acid in mesencephalic cultures: effects on dopaminergic neuron development. *J Neurochem* 57: 458–464.
25. Kroczek, R., and B.-W. Mages. (1994). DNA sequence encoding a novel member of the steroid and thyroid hormone receptor family. International Patent Application WO 94/04675.
26. Kujubu, D. A., R. W. Lim, B. C. Varnum, and H. R. Herschman. (1987) Induction of transiently expressed genes in PC-12 pheochromocytoma cells. *Oncogene* 1: 257–262.
27. Law, S. W., O. M. Conneely, and B. W. O'Malley. (1994) Molecular cloning of a novel member of the nuclear receptor superfamily related to the orphan receptor, TR2. *Gene Expr* 4: 77–84.
28. Lindvall, O., P. Brundin, B. Widner, S. Rehncrona, B. Gustavii, R. Frackowiak, K. L. Leenders, G. Sawle, J. C. Rothwell, C. D. Marsden, and et al. (1990) Grafts of fetal dopamine neurons survive and improve motor function in Parkinson's disease. *Science* 247: 574–577.
29. Lindvall, O., S. Rehncrona, P. Brundin, B. Gustavii, B. Astedt, B. Widner, T. Lindholm, A. Bjorklund, K. L. Leenders, J. C. Rothwell, and et al. (1989) Human fetal dopamine neurons grafted into the striatum in two patients with severe Parkinson's disease. A detailed account of methodology and a 6-month follow-up. *Arch Neurol* 46: 615–631.
30. Lindvall, O., H. Widner, S. Rehncrona, P. Brundin, P. Odin, B. Gustavii, R. Frackowiak, K. L. Leenders, G. Sawle, J. C. Rothwell, and et al. (1992) Transplantation of fetal dopamine neurons in Parkinson's disease: one-year clinical and neurophysiological observations in two patients with putaminal implants. *Ann Neurol* 31: 155–165.
31. Ling, Z. D., E. D. Potter, J. W. Lipton, and P. M. Carvey. (1998) Differentiation of mesencephalic progenitor cells into dopaminergic neurons by cytokines. *Exp Neurol* 149: 411–423.
32. Lisovoski, F., J. P. Wahrmann, J. C. Pages, J. Cadusseau, M. Rieu, A. Weber, A. Kahn, and M. Peschanski. (1997) Long-term histological follow-up of genetically modified myoblasts grafted into the brain. *Brain Res Mol Brain Res* 44: 125–133.
33. Mages, H. W., O. Rilke, R. Bravo, G. Senger, and R. A. Kroczek. (1994) NOT, a human immediate-early response gene closely related to the steroid/thyroid hormone receptor NAK1/TR3. *Mol Endocrinol* 8: 1583–1591.
34. Mayer, E., S. B. Dunnett, and J. W. Fawcett. (1993) Mitogenic effect of basic fibroblast growth factor on embryonic ventral mesencephalic dopaminergic neurone precursors. *Brain Res Dev Brain Res* 72: 253–258.
35. Milbrandt, J. (1988) Nerve growth factor induces a gene homologous to the glucocorticoid receptor gene. *Neuron* 1: 183–188.
36. Nakai, A., S. Kartha, A. Sakurai, F. G. Toback, and L. J. DeGroot. (1990) A human early response gene homologous to murine nur77 and rat NGFI-B, and related to the nuclear receptor superfamily. *Mol Endocrinol* 4: 1438–1443.
37. National Cancer Institute, C. G. A. P. (1997) Genbank submission: NCI_CGAP_Lu5 Homo sapiens cDNA clone IMAGE:1568227. Accession No.: AA932044.
38. Ohkura, N., M. Hijikuro, A. Yamamoto, and K. Miki. (1994) Molecular cloning of a novel thyroid/steroid receptor superfamily gene from cultured rat neuronal cells. *Biochem Biophys Res Commun* 205: 1959–1965.

39. Ohkura, N., M. Ito, T. Tsukada, K. Sasaki, K. Yamaguchi, and K. Miki. (1996) Structure, mapping and expression of a human NOR-1 gene, the third member of the Nur77/NGFI-B family. *Biochim Biophys Acta* 1308: 205–214.

40. Okabe, T., R. Takayanagi, K. Imasaki, M. Haji, H. Nawata, and T. Watanabe. (1995) cDNA cloning of a NGFI-B/nur77-related transcription factor from an apoptotic human T cell line. *J Immunol* 154: 3871–3879.

41. Olanow, C. W., J. B. Kordower, and T. B. Freeman. (1996) Fetal nigral transplantation as a therapy for Parkinson's disease. *Trends Neurosci* 19: 102–109.

42. Peña de Ortiz, S., and G. A. Jamieson, Jr. (1996) HZF-3, an immediate-early orphan receptor homologous to NURR1/NOT: induction upon membrane depolarization and seizures. *Brain Res Mol Brain Res* 38: 1–13.

43. Perrone-Capano, C., and U. di Porzio. (1996) Epigenetic factors and midbrain dopaminergic neurone development. *Bioessays* 18: 817–824.

44. Peschanski, M., G. Defer, J. P. N'Guyen, F. Ricolfi, J. C. Monfort, P. Remy, C. Geny, Y. Samson, P. Hantraye, R. Jeny, and et al. (1994) Bilateral motor improvement and alteration of L-dopa effect in two patients with Parkinson's disease following intrastriatal transplantation of foetal ventral mesencephalon. *Brain* 117: 487–499.

45. Petropoulos, I., D. Part, A. Ochoa, M. M. Zakin, and E. Lamas. (1995) NOR-2 (neuron-derived orphan receptor), a brain zinc finger protein, is highly induced during liver regeneration. *FEBS Lett* 372: 273–278.

46. Pichon, B., C. Jimenez-Cervantes, I. Pirson, C. Maenhaut, and D. Christophe. (1996) Induction of nerve growth factor-induced gene-B (NGFI-B) as an early event in the cyclic adenosine monophosphate response of dog thyrocytes in primary culture. *Endocrinology* 137: 4691–4698.

47. Placzek, M., T. Yamada, M. Tessier-Lavigne, T. Jessell, and J. Dodd. (1991) Control of dorsoventral pattern in vertebrate neural development: induction and polarizing properties of the floor plate. *Development* Suppl 2: 105–122.

48. Ptak, L. R., K. R. Hart, D. Lin, and P. M. Carvey. (1995) Isolation and manipulation of rostral mesencephalic tegmental progenitor cells from rat. *Cell Transplant* 4: 335–342.

49. Quinn, N. P. (1997) Parkinson's disease: clinical features. *Baillieres Clin Neurol* 6: 1–13.

50. Rabinovsky, E. D., J. Ramchatesingh, and J. L. McManaman. (1995) Regulation of tyrosine hydroxylase gene expression in IMR-32 neuroblastoma cells by basic fibroblast growth factor and ciliary neurotrophic factor. *J Neurochem* 64: 2404–2412.

51. Redmond, D. E., Jr., C. Leranth, D. D. Spencer, R. Robbins, T. Vollmer, J. B. Kim, R. B. Roth, A. J. Dwork, and F. Naftolin. (1990) Fetal neural graft survival [letter] [see comments]. *Lancet* 336: 820–822.

52. Ryseck, R. P., B. Macdonald-Bravo, M. G. Mattei, S. Ruppert, and R. Bravo. (1989) Structure, mapping and expression of a growth factor inducible gene encoding a putative nuclear hormonal binding receptor. *Embo J* 8: 3327–3335.

53. Saucedo-Cardenas, O., R. Kardon, T. R. Ediger, J. P. Lydon, and O. M. Conneely. (1997) Cloning and structural organization of the gene encoding the murine nuclear receptor transcription factor, NURR1. *Gene* 187: 135–139.

54. Saucedo-Cardenas, O., J. D. Quintana-Hau, W. D. Le, M. P. Smidt, J. J. Cox, F. De Mayo, J. P. Burbach, and O. M. Conneely. (1998) Nurr1 is essential for the induction of the dopaminergic phenotype and the survival of ventral mesencephalic late dopaminergic precursor neurons. *Proc Natl Acad Sci U S A* 95: 4013–4018.

55. Sawle, G. V., P. M. Bloomfield, A. Bjorklund, D. J. Brooks, P. Brundin, K. L. Leenders, O. Lindvall, C. D. Marsden, S. Rehncrona, H. Widner, and et al. (1992) Transplantation of fetal dopamine neurons in Parkinson's disease: PET [18F]6-L-fluorodopa studies in two patients with putaminal implants. *Ann Neurol* 31: 166–173.

56. Scearce, L. M., T. M. Laz, T. G. Hazel, L. F. Lau, and R. Taub. (1993) RNR-1, a nuclear receptor in the NGFI-B/Nur77 family that is rapidly induced in regenerating liver. *J Biol Chem* 268: 8855–8861.

57. Schapira, A. H. (1997) Pathogenesis of Parkinson's disease. *Baillieres Clin Neurol* 6: 15–36.

58. Smidt, M. P., H. S. van Schaick, C. Lanctot, J. J. Tremblay, J. J. Cox, A. A. van der Kleij, G. Wolterink, J. Drouin, and J. P. Burbach. (1997) A homeodomain gene Ptx3 has highly restricted brain expression in mesencephalic dopaminergic neurons. *Proc Natl Acad Sci U S A* 94: 13305–13310.

59. Spencer, D. D., R. J. Robbins, F. Naftolin, K. L. Marek, T. Vollmer, C. Leranth, R. H. Roth, L. H. Price, A. Gjedde, B. S. Bunney, and et al. (1992) Unilateral transplantation of human fetal mesencephalic tissue into the caudate nucleus of patients with Parkinson's disease [see comments]. *N Engl J Med* 327: 1541–1548.

60. Sutherland, J. D., T. Kozlova, G. Tzertzinis, and F. C. Kafatos. (1995) Drosophila hormone receptor 38: a second partner for Drosophila USP suggests an unexpected role for nuclear receptors of the nerve growth factor-induced protein B type. *Proc Natl Acad Sci U S A* 92: 7966–7970.

61. Unsicker, K., C. Suter-Crazzalora, and K. Krieglstein. (1996) Growth factor function in the development and maintenance of midbrain dopaminergic neurons: concepts, facts and prospects for TGF-beta. *Ciba Found Symp* 196: 70–80; discussion 80–74.

62. Wang, L. H., S. Y. Tsai, R. G. Cook, W. G. Beattie, M. J. Tsai, and B. W. O'Malley. (1989) COUP transcription factor is a member of the steroid receptor superfamily. *Nature* 340: 163–166.

63. Wang, M. Z., P. Jin, D. A. Bumcrot, V. Marigo, A. P. McMahon, E. A. Wang, T. Woolf, and K. Pang. (1995) Induction of dopaminergic neuron phenotype in the midbrain by Sonic hedgehog protein. *Nat Med* 1: 1184–1188.

64. Widner, H., J. Tetrud, S. Rehncrona, B. Snow, P. Brundin, B. Gustavii, A. Bjorklund, O. Lindvall, and J. W. Langston. (1992) Bilateral fetal mesencephalic grafting in two patients with parkinsonism induced by 1-methyl-4-phenyl-1,2,3,6-tetrahydropyridine (MPTP) [see comments]. *N Engl J Med* 327: 1556–1563.

65. Widner, H., J. Tetrud, S. Rehncrona, B. J. Snow, P. Brundin, A. Bjorklund, O. Lindvall, and J. W. Langston. (1993) Fifteen months' follow-up on bilateral embryonic mesencephalic grafts in two cases of severe MPTP-induced parkinsonism. *Adv Neurol* 60: 729–733.

66. Xiao, Q., S. O. Castillo, and V. M. Nikodem. (1996) Distribution of messenger RNAs for the orphan nuclear receptors Nurr1 and Nur77 (NGFI-B) in adult rat brain using in situ hybridization. *Neuroscience* 75: 221–230.

67. Xing, G., L. Zhang, L. Zhang, T. Heynen, X. L. Li, M. A. Smith, S. R. Weiss, A. N. Feldman, S. Detera-Wadleigh, D. M. Chuang, and R. M. Post. (1997) Rat nurr1 is prominently expressed in perirhinal cortex, and differentially induced in the hippocampal dentate gyrus by electroconvulsive vs. kindled seizures. *Brain Res Mol Brain Res* 47: 251–261.
68. Yamada, T., M. Placzek, H. Tanaka, J. Dodd, and T. M. Jessell. (1991) Control of cell pattern in the developing nervous system: polarizing activity of the floor plate and notochord. *Cell* 64: 635–647.
69. Ye, W., K. Shimamura, J. L. R. Rubenstein, M. A. Hynes, and A. Rosenthal. (1998) FGF and Shh signals control dopaminergic and serotonergic cell fate in the anterior neural plate. *Cell* 93: 755–766.
70. Zetterstrom, R. H., L. Solomin, L. Jansson, B. J. Hoffer, L. Olson, and T. Perlmann. (1997) Dopamine neuron agenesis in Nurr1-deficient mice. *Science* 276: 248–250.
71. Zetterstrom, R. H., R. Williams, T. Perlmann, and L. Olson. (1996) Cellular expression of the immediate early transcription factors Nurr1 and NGFI-B suggests a gene regulatory role in several brain regions including the nigrostriatal dopamine system. *Brain Res Mol Brain Res* 41: 111–120.

While the invention has been described in connection with what is presently considered to be the most practical and preferred embodiments, it is to be understood that the invention is not limited to the disclosed embodiments, but on the contrary is intended to cover various modifications and equivalent arrangements included within the spirit and scope of the appended claims.

Thus, it is to be understood that variations in the present invention can be made without departing from the novel aspects of this invention as defined in the claims. All patents and articles cited herein are hereby incorporated by reference in their entirety and relied upon.

TABLE 1

| Cell Source | pCMV flgNurr1 TH+ cells/well ± SEM | CMV eGFP TH+ cells/well ± SEM | N= |
|---|---|---|---|
| Ventral Midbrain | 62.0 ± 3.22 | 0.0 ± 0.0 | 3 |
| Dorsal Midbrain | 33.3 ± 4.41 | 0.0 ± 0.0 | 3 |
| Lateral Ganglionic Eminence | 143.3 ± 19.88 | 0.0 ± 0.0 | 3 |

What is claimed is:

1. A method for generating tyrosine hydroxylase expressing cells in a culture of mammalian CNS stem cells, comprising the steps of:

a) culturing mammalian CNS stem cells in vitro;

b) introducing a polynucleotide that encodes a transcriptional regulator into the mammalian CNS stem cells in the culture, wherein the polynucleotide encodes a transcriptional regulator selected from the group consisting of Nurr1, RNR-1, HZF-3, TINUR, and NOT, and wherein the polynucleotide is expressed;

c) incubating the mammalian CNS stem cells; and d) identifying tyrosine hydroxylase expressing cells in the culture.

2. The method of claim 1, wherein the polynucleotide encodes Nurr1.

3. The method of claim 1, further comprising incubating the mammalian CNS stem cells with an agonist of protein kinase A activity.

4. The method of claim 3, wherein the agonist of protein kinase A activity is selected from the group consisting of forskolin; 1,9-dideoxy-forskolin; 6-[[(2-carbethoxyethyl)amino]carbonyl]-forskolin; 6-acetyl-7-deacetyl-forskolin; 6-O-[3'-(piperidino)propionyl]-forskolin hydrochloride; 7-deacetyl-forskolin; 7-deacetyl-6-(N-acetylglycyl)-forskolin; 7-deacetyl-7-[O-(N-methylpiperazino)-g-butyryl]-forskolin, dihydrochloride; 7-deacetyl-7-O-hemisuccinyl-forskolin; 3',5' cyclic monophosphate (cAMP); 8-chloro-cAMP; 8-bromo cAMP; 8-(4-chloropheylthio)-cAMP; dibutyryl-cAMP; dioctanoyl-cAMP; N6-monobutyryl-cAMP; adenosine 3',5' cyclic monophosphorthioate, Sp-isomer; and 8-bromo-adenosine 3', 5' cyclic monophosphorthioate, Sp-isomer.

5. The method of claim 3, wherein the agonist of protein kinase A activity is forskolin.

6. The method of claim 1, wherein the mammalian CNS stem cells are selected from the group consisting of ventral midbrain, dorsal midbrain, lateral ganglionic eminence, hippocampus, cerebral cortex, striatum, septum, diencephalon, mesencephalon, hindbrain and spinal cord.

7. The method of claim 1, wherein the mammalian CNS stem cells are human CNS stem cells.

* * * * *